United States Patent
Ogino et al.

(10) Patent No.: US 6,906,074 B2
(45) Date of Patent: Jun. 14, 2005

(54) 2-PHENYLPIPERAZINE DERIVATIVES

(75) Inventors: Takashi Ogino, Osaka (JP); Yukari Konishi, Hyogo (JP); Kunihiko Higashiura, Hyogo (JP); Kazuhito Furukawa, Hyogo (JP)

(73) Assignee: Nippon Zoki Pharmaceutical Co., Ltd., Osaka (JP)

( * ) Notice: Subject to any disclaimer, the term of this patent is extended or adjusted under 35 U.S.C. 154(b) by 131 days.

(21) Appl. No.: 10/370,918

(22) Filed: Feb. 20, 2003

(65) Prior Publication Data

US 2003/0166616 A1 Sep. 4, 2003

(30) Foreign Application Priority Data

Feb. 22, 2002 (JP) ..................... 2002-045562

(51) Int. Cl.$^7$ ............... C07D 241/08; C07D 403/06; A61K 31/50; A61K 31/501
(52) U.S. Cl. ............. 514/253.01; 514/254.01; 514/254.05; 514/225.05; 514/255.03; 544/337; 544/360; 544/366; 544/372; 544/384; 544/389; 544/390; 544/391; 544/403
(58) Field of Search ............. 514/253.01, 254.01, 514/254.05, 255.02, 255.03; 544/337, 360, 366, 372, 384, 389, 390, 391, 403

(56) References Cited

U.S. PATENT DOCUMENTS

| | | | |
|---|---|---|---|
| 5,472,978 A | 12/1995 | Baker et al. | 514/443 |
| 5,610,183 A | 3/1997 | Owens et al. | 514/539 |
| 5,629,347 A | 5/1997 | Swain et al. | 514/620 |
| 5,719,156 A | 2/1998 | Shue et al. | 514/252.13 |
| 5,795,894 A | 8/1998 | Shue et al. | 514/254.04 |
| 5,798,359 A | 8/1998 | Shue et al. | 517/252.12 |
| 5,892,039 A | 4/1999 | Shue et al. | 544/360 |
| 5,981,520 A | 11/1999 | Shue et al. | 514/217.05 |

FOREIGN PATENT DOCUMENTS

| | | |
|---|---|---|
| GB | 2271774 A | 4/1994 |
| JP | 6509332 T | 1/1993 |
| JP | 6509087 T | 12/1995 |
| JP | 6509090 T | 3/1997 |
| WO | WO 01/70708 A1 | 9/2001 |

OTHER PUBLICATIONS

Chawla SP, Grunberg SM, Gralla RJ, Hesketh PJ, Rittenberg C, Elmer ME, Schmidt C, Taylor A, Carides AD, Evans JK, Horgan KJ., Cancer. May 1, 2003;97(9):2290–300.*

Ranga K, Krishnan R, J Clin Psychiatry. 2002; 63 Suppl 11:25–9, Medline abstract PMID: 12562140.*

West, Anthony R., Solid State Chemistry and its Applications, Wiley, New York, 1988, pp. 358 & 365.*

Williams et al., *Acyclic NK–1 Antagonists: 2–Benzhydryl–2–Aminoethyl Ethers*, Bioorganic & Medicinal Chemistry Letters, vol. 4, No. 16, pp. 1903–1908, 1994.

Stevenson et al., *4,4–Disubstituted Piperidine High–affinity $NK_1$ Antagonists: Structure—Activity Relationships and in Vivo Activity*, J. Med. Chem., 41, pp. 4623–4635, 1998.

Vedani et al., *Multiple–Conformation and Protonation–State Representation in 4D–QSAR: The Neurokinin–1 Receptor System*, J. Med. Chem., 43, pp. 4416–4427, 2000.

* cited by examiner

Primary Examiner—Thomas C. McKenzie
(74) Attorney, Agent, or Firm—Hollander Law Firm, P.L.C.

(57) ABSTRACT

A 2-phenylpiperazine derivative represented by the formula (I) or a pharmaceutically acceptable salt, hydrate, or complex thereof:

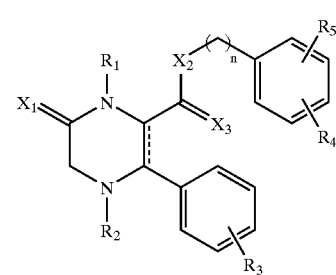

I wherein each of $X_1$ and $X_3$ is oxygen or two hydrogen atoms, $X_2$ O, NH, $NCH_3$, or $CH_2$, n is an integer of 0 or 1, $R_1$ is hydrogen or lower alkyl and $R_2$ is hydrogen, cyano, tetrazolyl, aminotriazolyl, mesyl, t-butoxycarbonyl, or a lower alkyl which may be optionally substituted, $R_3$ is hydrogen, halogen, lower alkyl or lower alkoxy, each of $R_4$ and $R_5$ is hydrogen, lower alkoxy or trifluoromethyl, and a broken line indicates a single or double bond. The derivative may be used as a tachykinin antagonist in the treatment of diseases of the digestive system, nervous system and respiratory system, inflammation, allergy, carcinoid syndrome, chronic pain, headache, Crohn disease, depression and vomiting.

18 Claims, No Drawings

2-PHENYLPIPERAZINE DERIVATIVES

FIELD OF THE INVENTION

The present invention relates to novel 2-phenylpiperazine derivatives and pharmaceutical compositions containing the derivatives as an effective component.

BACKGROUND OF THE INVENTION

Tachykinin is a general term for a group of peptides having similar structures. In mammals, Substance P (SP), neurokinin A (NKA) and neurokinin B (NKB) are representative tachykinins. These tachykinins are neuro-peptides which are widely distributed in a living body. Among them, Substance P has been most fully investigated for physiological functions. Substance P is a peptide consisting of 11 amino acids and exhibits hypotensive action, smooth muscle constricting action, sialagogue action, neuron exciting action, pain inducing action, etc. Substance P has been known to be concerned with various diseases such as those of the digestive system, nervous system and respiratory system. It has also been suggested to be deeply associated especially with inflammation, allergy, carcinoid syndrome, chronic pain, headache, Crohn disease, depression and vomiting. Accordingly, an antagonist for a tachykinin such as Substance P is applicable and useful as an anti-inflammatory agent, anti-allergic agent, analgesic, antiemetic, agent for irritable colon syndrome, agent for dermal disease, agent for vasospastic disease, agent for cerebral ischemic disease, antidepressant, antianxiety agent, agent for autoimmune disease, a muscle relaxant or an antispasmodic.

Various tachykinin antagonists have been developed and reported with an object of development of therapeutic agents for the above-mentioned diseases in which tachykinins participate (cf. Japanese Laid-Open Patent Publications Hei-06/509332, Hei-06/509087, Hei-06/509090, Bioorg. Med. Chem. Lett., 4, 16, 1903–1908 (1994), J. Med. Chem., 41, 4623–4635 (1998), J. Med. Chem., 43, 4416–4427 (2000) etc.). However, tachykinin antagonists which have heretofore been found have problems of performance in vivo such as undesirable transfer into blood and adverse effects, and none of them have been put into the market with approval as a pharmaceutical agent.

The present inventors have carried out intensive investigations for piperazine derivatives and have found novel 2-phenylpiperazine derivatives which have a good tachykinin antagonistic action and are useful as pharmaceutical agents, whereupon the present invention has been accomplished.

The present invention solves the above-mentioned problems and provides useful, novel compounds as tachykinin antagonists having high safety and a preferred behavior in vivo.

SUMMARY OF THE INVENTION

The 2-phenylpiperazine derivatives and their pharmaceutically acceptable salts of the present invention may be used in pharmaceutically effective amounts as an anti-inflammatory agent, an anti-allergic agent, an analgesic, an antiemetic, an agent for irritable colon syndrome, an agent for dermal disease, an agent for vasospastic disease, an agent for cerebral ischemic disease, an antidepressant, an antianxiety agent, an agent for autoimmune disease, a muscle relaxant or an antispasmodic. They may be used as therapeutic agents for the treatment of diseases associated with tachykinins in patients known to be in need of such treatment, or known to be in need of suppression of tachykinins. Thus, in embodiments of the present invention the 2-phenylpiperazine derivatives and their pharmaceutically acceptable salts may be used for treatment of tachykinin associated diseases such as those of the digestive system, nervous system and respiratory system, inflammation, allergy, carcinoid syndrome, chronic pain, headache, Crohn disease, depression and vomiting in patients known to be in need of such treatment.

The pharmaceutical compositions employed in the present invention include at least one 2-phenylpiperazine derivative represented by the general formula (I) or pharmaceutically acceptable salts of the derivatives represented by the general formula (I):

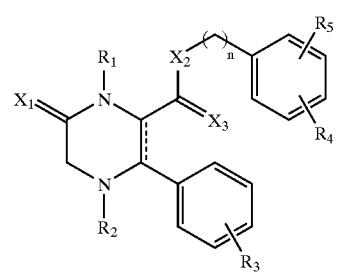

wherein each of $X_1$ and $X_3$ is oxygen or two hydrogen atoms, $X_2$ is O, NH, NCH$_3$, or CH$_2$, n is an integer of 0 or 1, $R_1$ is hydrogen or lower alkyl and $R_2$ is hydrogen, cyano, tetrazolyl, aminotriazolyl, mesyl, t-butoxycarbonyl, or lower alkyl, wherein when $R_2$ is lower alkyl, the lower alkyl may be optionally substituted with a substituent selected from the following substituents (a) to (j) and/or oxo, (a) triazolonyl,
(b) tetrazolyl,
(c) dimethylaminomethyltriazolyl;
(d) phosphotriazolonyl,
(e) pyridyl,
(f) dimethylamino,
(g) cyano,
(h) pyrrolidino,
(i) amino,
(j) phenyl, $R_3$ is hydrogen, halogen, lower alkyl or lower alkoxy, each of $R_4$ and $R_5$ is hydrogen, lower alkoxy or trifluoromethyl, and a broken line indicates a single or double bond.

The 2-phenylpiperazine derivatives and their pharmaceutically acceptable salts may be administered orally, parenterally, or intranasally to patients in need of treatment in pharmaceutically effective amounts with little, if any side effects, low toxicity, and high safety to substantially suppress tachykinin serum levels or values in patients diagnosed with a disease associated with tachykinins. The compounds of the present invention reduce the activity of tachykinins in blood by blocking their access to tachykinin receptors.

DETAILED DESCRIPTION OF THE INVENTION

The present invention relates to 2-phenylpiperazine derivatives represented by the following formula (I) and it further relates to a Substance P antagonist containing the compound as an effective component:

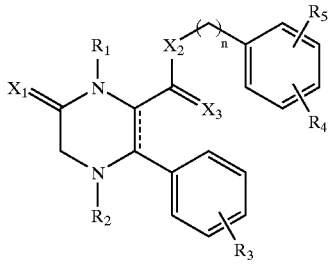

wherein each of $X_1$ and $X_3$ is oxygen or two hydrogen atoms, $X_2$ is O, NH, $NCH_3$ or $CH_2$, n is an integer of 0 or 1, $R_1$ is hydrogen or lower alkyl and $R_2$ is hydrogen, cyano, tetrazolyl, aminotriazolyl, mesyl, t-butoxycarbonyl, or lower alkyl, wherein when $R_2$ is lower alkyl, the lower alkyl may be unsubstituted, substituted with any one of the following substituents (a) to (j), substituted with only oxo, or substituted with both oxo and any one of the following substituents (a) to (j), (a) triazolonyl, (b) tetrazolyl, (c) dimethylaminomethyltriazolyl;

(d) phosphotriazolonyl, (e) pyridyl, (f) dimethylamino, (g) cyano, (h) pyrrolidino, (i) amino, (j) phenyl, $R_3$ is hydrogen, halogen, lower alkyl or lower alkoxy, each of $R_4$ and $R_5$ is hydrogen, lower alkoxy or trifluoromethyl and a broken line indicates a single or double bond. When the broken line represents a single bond, there is an H at each carbon atom.

In the above-mentioned formula (I), "lower alkyl" is preferably a linear or branched alkyl having 1 to 6 carbon atoms such as methyl, ethyl, propyl, isopropyl, butyl, isobutyl, sec-butyl or t-butyl, pentyl, isopentyl, neopentyl, t-pentyl, hexyl, isohexyl, dimethylbutyl, and more preferably a linear or branched alkyl having 1 to 4 carbon atoms.

Also, "lower alkoxy" is preferably a linear or branched alkoxy having 1 to 6 carbon atoms such as methoxy, ethoxy, propoxy, isopropoxy, butoxy, much more preferably a linear or branched alkoxy having 1 to 4 carbon atoms.

Preferred embodiments of the present invention are:

(1) A piperazine derivative represented by the above formula (I) and pharmaceutically acceptable salts and hydrates thereof.

(2) A piperazine derivative according to subparagraph (1) wherein $X_1$ is oxygen.

(3) A piperazine derivative according to subparagraph (2) wherein $X_2$ is oxygen.

(4) A piperazine derivative according to subparagraph (3) wherein $X_3$ is two hydrogen atoms.

(5) A piperazine derivative according to subparagraph (4) wherein n is an integer of 1.

(6) A piperazine derivative according to subparagraph (5) wherein $R_1$ is methyl.

(7) A piperazine derivative according to subparagraph (6) wherein $R_2$ is triazolonylmethyl.

(8) A piperazine derivative according to subparagraph (7) wherein $R_3$ is hydrogen.

(9) A piperazine derivative according to subparagraph (8) wherein $R_4$ is substituted at the m-position.

(10) A piperazine derivative according to subparagraph (9) wherein $R_4$ is trifluoromethyl.

(11) A piperazine derivative according to subparagraph (10) wherein $R_5$ is substituted at the m-position.

(12) A piperazine derivative according to subparagraph (11) wherein $R_5$ is trifluoromethyl.

(13) A medicine containing a piperazine derivative according to subparagraph (1) as an effective component.

(14) A medicine according to subparagraph (13), which is an anti-inflammatory agent, an anti-allergic agent, an analgesic, an antiemetic, an agent for irritable colon syndrome, an agent for dermal disease, an agent for vasospastic disease, an agent for cerebral ischemic disease, an antidepressant, an antianxiety agent, an agent for autoimmune disease, a muscle relaxant or an antispasmodic.

Preferred compounds of the present invention are:

Compound 1: (5R,6R)-6-(3,5-Bis(trifluoromethyl) benzyloxymethyl)-5-phenylpiperazin-2-one hydrochloride Compound 2: 6-(3-(3,5-Bis(trifluoromethyl)phenyl] propyl)-5-phenylpiperazin-(2-one hydrochloride Compound 3: 6-(3-(3,5-Bis(trifluoromethyl)phenyl) propyl)-4-(5-oxo-4,5-dihydro-1H-(1,2,4)triazol-3-ylmethyl)-5-phenylpiperazin-2-one Compound 4: 6-(3-(3,5-Bis(trifluoromethyl)phenyl) propyl)-5-phenyl-4-(4H-(1,2,4)triazol-3-ylmethyl) piperazin-2-one Compound 5: (5S,6S)-6-(3,5-Bis(trifluoromethyl) benzyloxymethyl)-5-phenylpiperazin-2-one hydrochloride Compound 6: (5S,6R)-6-(2-(2-Methoxyphenyl)ethyl)-5-phenylpiperazin-2-one hydrochloride Compound 7: (5S,6S)-6-(2-(2-Methoxyphenyl)ethyl)-5-phenylpiperazin-2-one hydrochloride Compound 8: (5S,6S)-2-(3,5-Bis(trifluoromethyl) benzyloxymethyl)-3-phenylpiperazine dihydrochloride Compound 9: (5S,6R)-2-Phenethyl-3-phenylpiperazine dihydrochloride Compound 10: (5S,6S)-2-(2-(2-Methoxyphenyl)ethyl)-3-phenylpiperazine dihydrochloride Compound 11: (5S,6S)-6-(2-Methoxyphenoxymethyl)-5-phenylpiperazin-2-one hydrochloride Compound 12: (5S,6S)-6-(3,5-Bis(trifluoromethyl) benzyloxymethyl)-4-(5-oxo-4,5-dihydro-1H-(1,2,4)triazol-3-ylmethyl)-5-phenylpiperazin-2-one Compound 13: tert-Butyl 5-((3,5-bis(trifluoromethyl) benzyl)methylcarbamoyl)-4-methyl-3-oxo-6-phenyl-3,4-dihydro-2H-pyrazine-1-carboxylate Compound 14: (5S,6S)-4-(5-Amino-1H-(1,2,4)triazol-3-yl)-6-(3,5-bis(trifluoromethyl)benzyloxymethyl)-5-phenylpiperazin-2-one Compound 15: (5S,6S)-6-(3,5-bis(trifluoromethyl) benzyloxymethyl)-5-phenyl-4-(2-pyrrolidin-1-ylacetyl) piperazin-2-one hydrochloride Compound 16: (5S,6S)-2-(3-(3,5-Bis(trifluoromethyl) benzyloxymethyl)-5-oxo-2-phenylpiperazin-1-yl)acetamide hydrochloride Compound 17: (5S,6S)-(3-(3,5-Bis(trifluoromethyl) benzyloxymethyl)-5-oxo-2-phenylpiperazin-1-yl) acetonitrile hydrochloride Compound 18: (5S,6S)-3-(3,5-Bis(trifluoromethyl) benzyloxymethyl)-5-oxo-2-phenylpiperazine-1-carbonitrile Compound 19: (5S,6S)-6-(3,5-Bis(trifluoromethyl) benzyloxymethyl)-5-phenyl-4-(2H-tetrazol-5-yl)piperazin-2-one Compound 20: (5S,6S)-6-(3,5-Bis(trifluoromethyl) benzyloxymethyl)-4-(2-dimethylaminoacetyl)-5-phenylpiperazin-2-one Compound 21: (5S,6S)-6-(3,5-Bis(trifluoromethyl)benzyloxymethyl)-5-phenyl-4-(4H-(1,2,4)triazol-3-ylmethyl)piperazin-2-one Compound 22: (5S,6S)-6-(3,5-Bis(trifluoromethyl)benzyloxymethyl)-5-phenyl-4-(2-pyridin-4-ylacetyl)piperazin-2-one Compound 23: (5S,6S)-6-(3,5-Bis(trifluoromethyl)benzyloxymethyl)-4-methanesulfonyl-5-phenylpiperazin-2-one Compound 24: (5S,6S)-6-(3,5-Bis(trifluoromethyl)benzyloxymethyl)-1-methyl-5-phenylpiperazin-2-one hydrochloride Compound 25: (5S,6S)-6-(3,5-Bis(trifluoromethyl)benzyloxymethyl)-4-(5-dimethylaminomethyl-1H-(1,2,3)triazol-4-ylmethyl)-5-phenylpiperazin-2-one dihydrochloride Compound 26: (5S,6S)-6-(3,5-Bis(trifluoromethyl)benzyloxymethyl)-1-methyl-4-(5-oxo-4,5-dihydro-1H-(1,2,4)triazol-3-ylmethyl)-5-phenylpiperazin-2-one Compound 27: (5R,6R)-6-(3,5-Bis(trifluoromethyl)benzyloxymethyl)-4-(5-oxo-4,5-dihydro-1H-(1,2,4)triazol-3-ylmethyl)-5-phenylpiperazin-2-one Compound 28: 6-Oxo-3-phenyl-1,4,5,6-tetrahydropyrazine-2-carboxylic acid (3,5-bis(trifluoromethyl)benzyl)methylamide Compound 29: (5R,6R)-4-Benzyl-6-(3,5-bis(trifluoromethyl)benzyloxymethyl)-5-phenylpiperazin-2-one Compound 30: (5S,6S)-6-(3,5-Bis(trifluoromethyl)benzyloxymethyl)-5-(4-fluorophenyl)piperazin-2-one Compound 31: (2R,3R)-1-Benzyl-3-(3,5-bis(trifluoromethyl)benzyloxymethyl)-2-phenylpiperazine dihydrochloride Compound 32: (5S,6S)-6-(3,5-Bis(trifluoromethyl)benzyloxymethyl)-5-(4-fluorophenyl)-4-(5-oxo-4,5-dihydro-1H-(1,2,4)triazol-3-ylmethyl)piperazin-2-one Compound 33: (5S,6S)-6-(3,5-Bis(trifluoromethyl)benzyloxymethyl)-5-(4-methylphenyl)piperazin-2-one Compound 34: (5S,6S)-6-(3,5-Bis(trifluoromethyl)benzyloxymethyl)-4-(5-oxo-4,5-dihydro-1H-(1,2,4)triazol-3-ylmethyl)-5-(4-methylphenyl)piperazin-2-one Compound 35: (5S,6S)-5-(3-(3,5-Bis(trifluoromethyl)benzyloxymethyl)-2-phenylpiperazin-1-ylmethyl)-2,4-dihydro-(1,2,4)triazol-3-one dihydrochloride Compound 36: (5S,6S)-6-(3,5-Bis(trifluoromethyl)benzyloxymethyl)-5-(4-fluorophenyl)-1,3-dimethylpiperazin-2-one hydrochloride Compound 37: (5S,6S)-6-(3,5-Bis(trifluoromethyl)benzyloxymethyl)-5-(4-fluorophenyl)-1-methylpiperazin-2-one hydrochloride Compound 38: (5S,6S)-6-(3,5-Bis(trifluoromethyl)benzyloxymethyl)-5-(4-fluorophenyl)-1-methyl-4-(5-oxo-4,5-dihydro-1H-(1,2,4)triazol-3-ylmethyl)piperazin-2-one Compound 39: (5S,6S)-6-(3,5-Bis(trifluoromethyl)benzyloxymethyl)-4-(5-dimethylaminomethyl-1H-(1,2,3)triazol-4-ylmethyl)-5-(4-fluorophenyl)piperazin-2-one dihydrochloride Compound 40: (5S,6S)-6-(3,5-Bis(trifluoromethyl)benzyloxymethyl)-5-(4-fluorophenyl)-4-(5-oxo-4,5-dihydro-1H-(1,2,4)triazol-3-ylmethyl)piperazin-2-one Compound 41: (5S,6S)-6-(3,5-Bis(trifluoromethyl)benzyloxymethyl)-4-(5-dimethylaminomethyl-1H-(1,2,3)triazol-4-ylmethyl)-5-(4-fluorophenyl)-1-methylpiperazin-2-one dihydrochloride Compound 42: (5S,6S)-3-(6-(3,5-bis(trifluoromethyl)benzyloxymethyl)-2-oxo-5-phenylpiperazin-4-ylmethyl)-5-oxo-4,5-dihydro-(1,2,4)triazol-1-yl)phosphoric acid, bis(N-methyl-D-glucamine)

(2S,3S)-(3-(3-(3,5-Bis(trifluoromethyl)benzyloxymethyl)-5-oxo-2-phenylpiperazin-1-ylmethyl)-5-oxo-4,5-dihydro-(1,2,4)triazol-1-yl)phosphonic acid bis(N-methyl-D-glucamine)

Compound 43: (5S,6S)-6-(3,5-Bis(trifluoromethyl)benzyloxymethyl)-1-methyl-4-(5-oxo-4,5-dihydro-1H-(1,2,4)triazol-3-ylmethyl)-5-(4-methylphenyl)piperazin-2-one Compound 44: (5S,6S)-6-(3,5-Bis(trifluoromethyl)benzyloxymethyl)-1-ethyl-4-(5-oxo-4,5-dihydro-1H-(1,2,4)triazol-3-ylmethyl)-5-(4-methylphenyl)piperazin-2-one Compound 45: (5S,6S)-6-(3,5-Bis(trifluoromethyl)benzyloxymethyl)-1-ethyl-5-(4-fluorophenyl)-4-(5-oxo-4,5-dihydro-1H-(1,2,4)triazol-3-ylmethyl)piperazin-2-one Compound 46: (5S,6S)-6-(3,5-Bis(trifluoromethyl)benzyloxymethyl)-5-(4-fluorophenyl)-4-(5-oxo-4,5-dihydro-1H-(1,2,4)triazol-3-ylmethyl)-1-propylpiperazin-2-one Compound 47: (5S,6S)-6-(3,5-Bis(trifluoromethyl)benzyloxymethyl)-5-(4-isopropylphenyl)-1-methyl-4-(5-oxo-4,5-dihydro-1H-(1,2,4)triazol-3-ylmethyl)piperazin-2-one Compound 48: (5S,6S)-6-(3,5-Bis(trifluoromethyl)benzyloxymethyl)-5-(4-methoxyphenyl)-1-methyl-4-(5-oxo-4,5-dihydro-1H-(1,2,4)triazol-3-ylmethyl)piperazin-2-one Compound 49: (5S,6S)-6-(3,5-Bis(trifluoromethyl)benzyloxymethyl)-1-ethyl-4-(5-oxo-4,5-dihydro-1H-(1,2,4)triazol-3-ylmethyl)-5-phenylpiperazin-2-one Compound 50: (5S,6S)-6-(3,5-Bis(trifluoromethyl)benzyloxymethyl)-1-methyl-4-(5-oxo-4,5-dihydro-1H-(1,2,4)triazol-3-ylmethyl)-5-(3-methylphenyl)piperazin-2-one Compound 51: (5S,6S)-6-(3,5-Bis(trifluoromethyl)benzyloxymethyl)-5-(4-ethylphenyl)-1-methyl-4-(5-oxo-4,5-dihydro-1H-(1,2,4)triazol-3-ylmethyl)piperazin-2-one Compound 52: (5S,6S)-6-(3,5-Bis(trifluoromethyl)benzyloxymethyl)-1-ethyl-5-(4-methoxyphenyl)-4-(5-oxo-4,5-dihydro-1H-(1,2,4)triazol-3-ylmethyl)piperazin-2-one Of the above compounds of the present invention, the most preferred compound having the strongest action is Compound 26: (5S,6S)-6-(3,5-Bis(trifluoromethyl)benzyloxymethyl)-1-methyl-4-(5-oxo-4,5-dihydro-1H-(1,2,4)triazol-3-ylmethyl)-5-phenylpiperazin-2-one.

The compounds of the present invention represented by the formula (I) may be generally produced in the following manner wherein the substituents are defined as in formula (i) above unless indicated to the contrary:

The compounds of formula (I) may be obtained by alkylation, amidation or cross-coupling reaction of the compounds of formula (II). For example, the alkylation is carried out by using halogenated or mesylated compounds in the presence of a base, for example, a salt of an alkali metal or alkaline-earth metal such as potassium carbonate. It is possible to perform the condensing reaction by a general amidation method. For example, a method using a condensing agent such as 1,3-dicyclohexylcarbodiimide or WSC—HCl, mixed anhydride method or activated ester method may be employed. The reactions may be carried out in an appropriate solvent such as DMF, water, acetone or mixture thereof at a preferred temperature from room temperature to the boiling point of the solvent:

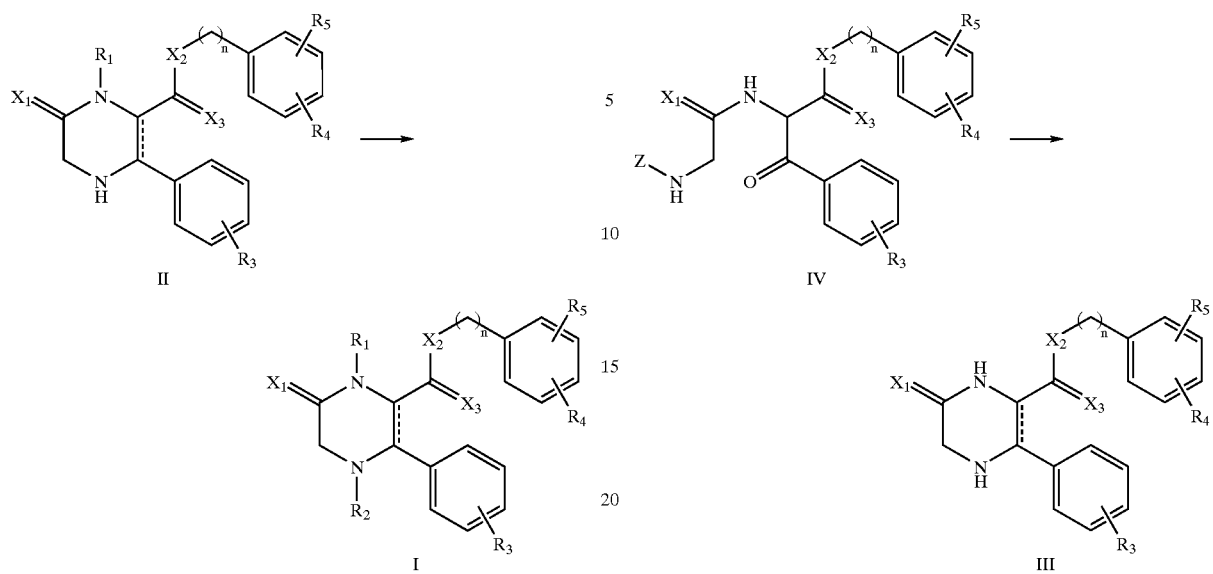

The compounds of formula (II) may be synthesized by an alkylation of the compounds of formula (III). To obtain the objective compound more selectively, it is preferred to protect an amino group by a protecting group such as a t-butoxycarbonyl group, and then an amido portion may be alkylated. The alkylating reaction may be carried out in the presence of a base such as sodium hydride in an appropriate solvent such as DMF, THF or mixture thereof at a preferred temperature from −20° C. to the boiling temperature of the solvent:

The compounds of formula (IV) may be synthesized by a dehydrating-condensation reaction between the benzoylamino compounds of formula (V) and benzyloxycarbonyl (Z)-glycine. It is possible to do the condensing reaction by a general amidation method, for example, a method using a condensing agent such as 1,3-dicyclohexylcarbodiimide or WSC—HCl, mixed anhydride method or activated ester method. The reactions may be carried out in an appropriate solvent such as acetic acid, THF, ether, DMF, dichloromethane, chloroform, dichloroethane or mixture thereof at a preferred temperature from room temperature to the boiling point of the solvent:

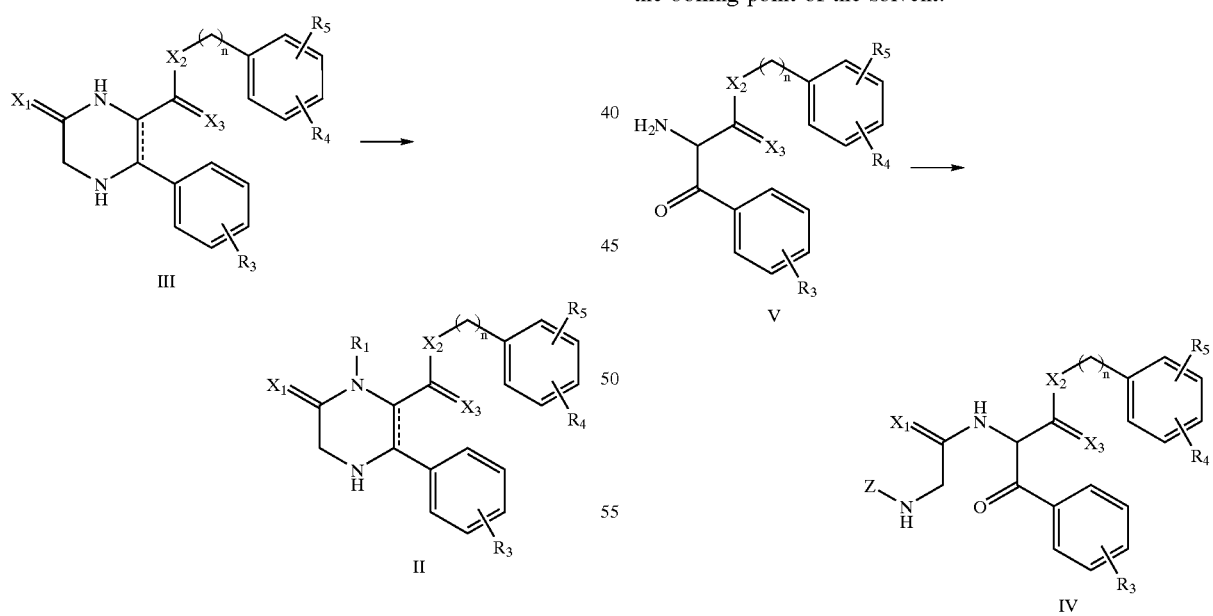

The compounds of formula (III) may be synthesized by catalytic reduction of the compounds of formula (IV), preferably, in the presence of a reduction catalyst such as palladium, palladium hydroxide or platinum oxide under an atmosphere of hydrogen. This reaction may be carried out in an appropriate solvent such as acetic acid, methanol, ethanol or mixture thereof at a preferred temperature from room temperature to the boiling point of the solvent:

The compounds of formula (V) may be synthesized by a reaction between a Weinreb-amido compound of formula (VI) and a nucleophilic reagent. To obtain the objective compound more selectively, it is preferred to protect an amino group by a protecting group such as a t-butoxycarbonyl group, and then an amido portion may be phenylated, preferably, reacted with phenyl-lithium reagent or Grignard reagent such as functionalized-phenylmagnesium bromide. The phenylating reaction may be carried out in an appropriate solvent such as THF, ether or mixture thereof at a preferred temperature from −78° C. to the boiling temperature of the solvent:

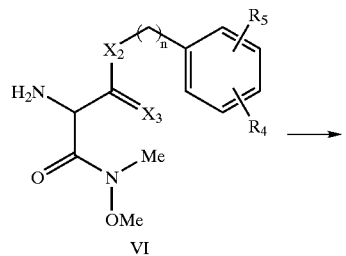

The Weinreb-amido compound of formula (VI) may be synthesized by a dehydrating-condensation reaction between a serine derivative of formula (VII) and methoxymethylamine. To obtain the objective compound more selectively, it is preferred to protect an amino group by a protecting group such as a t-butoxycarbonyl group, and then the reaction of the carboxy group portion may be performed. The condensing reaction may be carried out by a general amidation method, for example, a method using a condensing agent such as 1,3-dicyclohexylcarbodiimide or WSC—HCl, mixed anhydride method or activated ester method, preferably, in an appropriate solvent such as ethyl acetate, THF, ether, DMF, dichloromethane, chloroform, dichloroethane or mixture thereof at a preferred temperature from room temperature to the boiling point of the solvent:

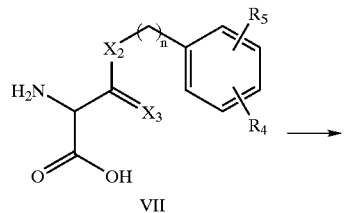

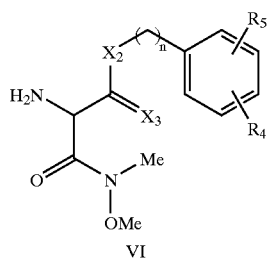

The serine derivative of formula (VII) may be synthesized by an alkylation, dehydrating-condensation reaction or cross-coupling reaction between a serine derivative of formula (VIII) and a functionalized-benzene derivative. To obtain the objective compound more selectively, it is preferred to protect an amino group by a protecting group such as a t-butoxycarbonyl group, and then the reaction may be performed. The alkylating reaction may be carried out by using halogenated or mesylated compounds in the presence of a base, for example, a salt of an alkali metal or alkaline-earth metal such as potassium carbonate. The condensing reaction may be carried out by a general amidation method, for example, a method using a condensing agent such as 1,3-dicyclohexylcarbodiimide or WSC—HCl, mixed anhydride method or activated ester method. Preferably, the reactions may be carried out in an appropriate solvent such as ethyl acetate, THF, ether, DMF, dichloromethane, chloroform, dichloroethane or mixture thereof at a preferred temperature from room temperature to the boiling point of the solvent:

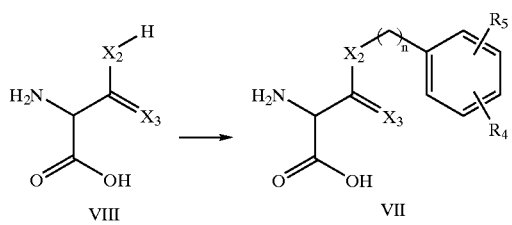

As to the serine derivative of formula (VIII), it is serine when $X_2=O$ and $X_3=H_2$, or it is aminomalonic acid when $X_2=O$ and $X_3=O$.

The 2-phenylpiperazine derivatives of the present invention include the pharmaceutically acceptable salts of the compounds represented by the above-given formula (I). Exemplary salts of the present invention are acid addition salts of the 2-phenylpiperazine derivatives of formula (I) with hydrochloric acid, sulfuric acid, nitric acid, hydrobromic acid, phosphoric acid, perchloric acid, thiocyanic acid, boric acid, formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, p-toluenesulfonic acid, naphthalenesulfonic acid or sulfanilic acid. Other salts of the present invention include salts of the 2-phenylpiperazine derivatives of formula (I) with: a) an alkali metal such as sodium or potassium, b) an alkaline-earth metal such as calcium or magnesium, c) other metals such as aluminum, or d) bases such as ammonia or organic amines.

The pharmaceutically acceptable salts may be manufactured by conventional methods starting from the 2-phenylpiperazine derivatives of formula (I) in a free state or free form, or by conversion from one salt to another salt.

When there are steric isomers or stereoisomers such as cis-trans isomers, optical isomers and conformational isomers, hydrates or metal complexes for the derivatives of the present invention, the present invention includes any and all of such isomers, hydrates, and complexes.

The compounds of the present invention, which include the 2-phenylpiperazine derivatives and their pharmaceutically acceptable salts, hydrates, isomers, and complexes, can be made into pharmaceutical preparations by combining one or more of the compounds with at least one pharmaceutically acceptable carrier or diluent. Any of the known methods for providing preparations, such as for oral or parenteral administrations (e.g. solids, semi-solids, liquids, gases, etc.) may be used to produce the pharmaceutical compositions of the present invention. For example, for oral administrations tablets, capsules, powders, liquids, etc. may be employed.

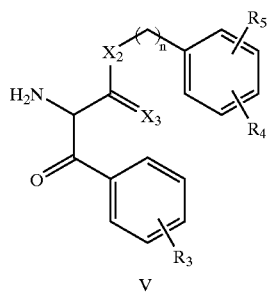

Parenteral administrations may be subcutaneous, intravenous, intramuscular, intrarectal and intranasal administrations.

In preparing the preparations, the 2-phenylpiperazine derivatives of the present invention may be used in the form of their pharmaceutically acceptable salts. The compounds of the present invention may be used either solely or jointly in pharmaceutically effective amounts for treating animals or humans. The compounds of the invention can be used either solely or jointly together in pharmaceutically acceptable amounts with pharmaceutically effective amounts of other pharmaceutically active components in pharmaceutical compositions or preparations.

In the case of preparations for oral administration, one or more of the compounds of the present invention either alone or in combination with commonly-used pharmaceutically acceptable excipients in pharmaceutically acceptable amounts such as at least one suitable pharmaceutically acceptable additive or carrier (e.g. lactose, mannitol, corn starch, potato starch, potassium citrate, etc.) may be mixed with one or more pharmaceutically acceptable: (1) binders such as cellulose derivatives (e.g. crystalline cellulose, hydroxypropylcellulose, etc.), gum arabicum, corn starch, gelatin, etc., (2) disintegrating agents such as corn starch, potato starch, calcium carboxymethylcellulose, etc., (3) lubricating agents such as talc, magnesium stearate, etc. and (4) other pharmaceutically acceptable excipients including pharmaceutically acceptable bulking agents, moisturizing agents, buffers, preservatives, perfumes and the like to obtain tablets, diluted powders, granules or capsules.

In embodiments of the invention, suppositories may be prepared by admixing one or more of the compounds of the present invention with pharmaceutically acceptable amounts of one or more pharmaceutically acceptable fatty/oily bases (e.g. cacao butter), emulsified bases, water-soluble bases (e.g. macrogol), hydrophilic bases, etc.

In the case of injections, it is possible to prepare solutions or suspensions of one or more compounds of the present invention in pharmaceutically acceptable carriers such as an aqueous or nonaqueous solvent. Examples of solvents which may be used are distilled water for injection, physiological saline solution, Ringer's solution, plant oil, synthetic fatty acid glycerides, higher fatty acid esters, propylene glycol, etc.

When the compounds of the present invention are used as inhalations or aerosol preparations, at least one compound of the present invention in the form of a liquid or minute powder can be filled up in an aerosol container with a gas or liquid spraying agent, and if desired, with conventional adjuvants such as one or more pharmaceutically acceptable humidifying agents or dispersing agents. They can also be used as pharmaceuticals for a non-pressurized preparation such as in a nebulizer or an atomizer.

It is also possible, depending upon the type of the disease, to prepare pharmaceutical preparations other than the above-mentioned ones which are suitable for therapy depending upon the state of the patient. Exemplary of other pharmaceutical preparations are collyriums, ointments, poultices, etc.

The preferred dosage of the compound of the present invention may vary depending upon the subject to be administered (age, body weight, symptons, etc. of the patient), form of the preparation, method for the administration, term for the administration, etc. To achieve a desired effect, 0.5–1000 mg per day, preferably 1–500 mg per day may be usually given to common adults by the oral route either once daily or several times a day. In the case of a parenteral administration such as by injection, the preferred dosage may be at a level of from ⅓ to ⅒ of the above-mentioned oral dosages because of the effects of absorption, etc. in the oral route.

The present invention is illustrated by the following non-limiting examples wherein all parts, percentages and ratios are by weight, all temperatures are at room temperature or in ° C., and all pressures are atmospheric unless indicated to the contrary:

EXAMPLES

The starting materials may be purchased from Aldrich Chemical Co., Inc. or Tokyo Kasei K.K. etc. The sample was placed in a glass capillary and the melting point was measured by a Yamato MP-21 melting point apparatus. $^1$H-NMR spectra were recorded on a Burker ARX-500 spectrometer and chemical shifts were reported as δ values (ppm) relative to TMS (δ=0 ppm) added as an internal standard. Silica gel column chromatography was carried out on BW-127ZH (Fuji-Silysia chemical Co., Ltd.). Thin-layer chromatography (TLC) was performed on silica gel F254 plates (Merck, No. 5715) visualized with UV light and 5% phosphomolybdic acid—EtOH reagent. Reagents and solvents were used in the commercially available grade without further purification.

Example 1

(A) Manufacture of (2R)-3-(3,5-bis(trifluoromethyl) benzyloxy)-2-tert-butoxycarbonylaminopropionic Acid D-serine (25 g, 238 mmol) and triethylamine (35 mL, 250 mmol) were dissolved in water (400 mL), and Boc$_2$O (50 g, 230 mmol) was added thereto and stirred at room temperature for 20 hours. The reaction mixture was washed with ethyl acetate (200 mL×2). The aqueous layer was acidified with 2 mol/L HCl to pH 2 and extracted with ethyl acetate (200 mL×5). The organic extract was dried over sodium sulfate anhydride. Sodium sulfate was filtered off and the solvent was removed by evaporation under reduced pressure to give Boc-D-Ser (44.4 g, 91%) as a colorless oil. Resulting Boc-D-Ser (44.4 g, 216 mmol) was dissolved in DMF (500 mL) and the mixture was cooled in an ice bath to 0° C. and then, NaH (18.4 g, 460 mmol) was added thereto in several portions. The mixture was stirred at 0° C. for 2 hours, and a solution of 3,5-bis(trifluoromethyl)benzyl bromide (42 mL, 230 mmol) in DMF (100 mL) was added dropwise thereto for a period of 30 min. After stirring at 0° C. for 2 hours and at room temperature for 20 hours, the reaction was stopped by adding water (1 L) thereto. The mixture was washed with hexane (250 mL×2) and acidified with 2 mol/L HCl to pH 2. After extracting with ethyl acetate (250 mL×4), the organic extract was washed with water and saturated brine in order and dried over sodium sulfate anhydride. Sodium sulfate was filtered off and the solvent was removed by evaporation under reduced pressure to give (2R)-3-(3,5-bis(trifluoromethyl)benzyloxy)-2-tert-butoxycarbonylaminopropionic acid (76.6 g, 82%) as a pale brown oil.

$^1$H-NMR (DMSO-d$_6$) δ: 1.39 (s, 9H), 3.73–3.79 (m, 2H), 4.25–4.29 (m, 1H), 4.65–4.73 (m, 2H), 7.12 (d, J=8.4 Hz, 1H), 7.96–8.03 (m, 3H), 12.65 (brs, 1H).

(B) Manufacture of (2R)-3-(3,5-bis(trifluoromethyl) benzyloxy)-2-tert-butoxycarbonylamino-N-methoxy-N-methyl-propionamide To a solution of (2R)-3-{3,5-bis(trifluoromethyl) benzyloxy}-2-tert-butoxycarbonylaminopropionic acid (76.6 g, 176 mmol), N-methoxy-N-methylamine hydrochloride (18.53 g, 190 mmol) and triethylamine (25.6 mL, 190 mmol) in CH$_2$Cl$_2$ (400 mL) was added WSC.HCl (36.4 g, 190 mmol). The mixture was stirred at room temperature for 20 hours, washed with water and saturated brine in order. The organic extract was dried over sodium sulfate anhydride. Sodium sulfate was filtered off and the solvent was removed by evaporation from the filtrate under reduced pressure to give (2R)-3-(3,5-bis(trifluoromethyl) benzyloxy)-2-tert-butoxycarbonylamino-N-methoxy-N-methylpropionamide (76.4 g, 92%) as a pale brown oil.

$^1$H-NMR (DMSO-d$_6$) δ: 1.37 (s, 9H), 3.11 (s, 3H), 3.60–3.68 (m, 2H), 3.73 (s, 3H), 4.68 (s, 2H), 4.79 (s, 1H), 7.13 (d, J=8.2 Hz, 1H), 8.01 (s, 3H).

(C) Manufacture of (2R)-3-(3,5-bis(trifluoromethyl) benzyloxy)-2-((2-(benzyloxycarbonyl)aminoacetyl)amino)-N-methoxy-N-methylpropionamide To a solution of (2R)-3-(3,5-bis(trifluoromethyl) benzyloxy)-2-tert-butoxycarbonylamino)-N-methoxy-N-methylpropionamide (76.4 g, 161 mmol) in 1,4-dioxane (200 mL) was added 4 mol/L HCl-1,4-dioxane (200 mL, 800 mmol). After stirring the mixture at room temperature for 2 hours, the solvent was removed by evaporation under reduced pressure. The oil residue was dissolved in CH$_2$Cl$_2$ (400 mL) and then, N-benzyloxycarbonylglycine (35.56 g, 170 mmol), triethylamine (24.0 mL, 170 mmol) and WSC.HCl (32.58 g, 170 mmol) were added thereto. The reaction mixture was stirred at room temperature for 20 hours, washed with saturated NH$_4$Cl and saturated brine in order. The organic layer was dried over sodium sulfate anhydride. Sodium sulfate was filtered off and the solvent was removed by evaporation from the filtrate under reduced pressure. The residue was purified on a silica gel column chromatography (CHCl$_3$: MeOH=49:1) to give (2R)-3-(3,5-bis(trifluoromethyl)benzyloxy)-2-tert-butoxycarbonylamino)-N-methoxy-N-methylpropionamide (74.5 g, 82%) as a yellow brown oil.

$^1$H-NMR (DMSO-d$_6$) δ: 3.13 (brs, 3H), 3.62–3.73 (m, 5H), 4.71 (s, 2H), 5.03 (s, 2H), 5.14 (brs, 1H), 7.30–7.43 (m, 6H), 8.00 (s, 2H), 8.02 (s, 1H), 8.30 (d, J=8.2 Hz, 1H).

(D) Manufacture of 2-Benzyloxycarbonylamino-N-((2R)-3-(3,5-bis(trifluoromethyl)benzyloxy)-1-phenyl-1-propanon-2-yl)acetamide To an ice cooled solution of Grignard reagent in THF (200 mL) prepared from magnesium (13.1 g, 540 mmol) and bromobenzene (57 mL, 540 mmol) was added dropwise a solution of (2R)-3-(3,5-bis(trifluoromethyl)benzyloxy)-2-((2-(benzyloxycarbonyl)aminoacetyl)amino)-Nmethoxy-N-methylpropionamide (76.34 g, 135 mmol) in THF (150 mL). After finishing the dropping, the reaction mixture was stirred at room temperature for 2 hours and poured into saturated NH$_4$Cl solution (500 mL). The mixture was extracted with ethyl acetate (200 mL×3) and then, the organic extract was washed with water and saturated brine in order and dried over sodium sulfate anhydride. Sodium sulfate was filtered off and the solvent was removed by evaporation from the filtrate under reduced pressure. The crude residue was recrystalized from ethyl acetate-ether-petroleum to give 2-benzyloxycarbonylamino-N-((2R)-3-(3,5-bis (trifluoromethyl)benzyloxy)-1-phenyl-1-propanon-2-yl) acetamide (33.83 g, 43%).

$^1$H-NMR (DMSO-d$_6$) δ: 3.66–3.71 (m, 2H), 3.84 (d, J=5.3 Hz, 2H), 4.62 (d, J=13.2 Hz, 1H), 4.67 (d, J=13.2 Hz, 1H), 5.02 (s, 2H), 5.63–5.66 (m, 1H), 7.30–7.36 (m, 5H), 7.46–7.53 (m, 3H), 7.64–7.67 (m, 1H), 7.86 (s, 2H), 7.97–8.00 (m, 3H), 8.48 (d, J=7.6 Hz, 1H).

(E) Manufacture of (5S,6S)-6-(3,5-bis(trifluoromethyl) benzyloxymethyl)-5-phenylpiperazin-2-one hydrochloride (Compound 5)

A mixture of 2-benzyloxycarbonylamino-N-((2R)-3-(3,5-bis(trifluoromethyl)benzyloxy)-1-phenyl-1-propanon-2-yl) acetamide (22 g, 49 mmol) and 5% palladium on carbon catalyst (2 g) in EtOH (400 mL) was stirred under a hydrogen atmosphere for 8 hours. The catalyst was filtered off and the filtrate was concentrated under reduced pressure. The residue was purified on a silica gel column chromatograph (CHCl$_3$:MeOH=10:1) and crystalized as a hydrochloride by adding 4 mol/L HCl-1,4-dioxane (1.5 mL). The crystals were filtered and dried to give (5S,6S)-6-(3,5-bis (trifluoromethyl)benzyloxymethyl)-5-phenylpiperazin-2-one hydrochloride (Compound 5) (13 g, 88%) as white crystals.

Mp. 219–221° C. (α)$_D$=99.7°(c1, MeOH). $^1$H-NMR (DMSO-d$_6$) δ: 3.36–3.42 (m, 2H), 3.71 (d, J=16.7 Hz, 1H), 3.90–3.99 (m, 2H), 4.57 (s, 2H), 5.00 (s, 1H), 7.35–7.41 (m, 3H), 7.48–7.50 (m, 2H), 7.97 (s, 2H), 8.01 (s, 1H), 8.77 (s, 1H), 9.74 (brs, 1H), 10.76 (brs, 1H).

(F) Manufacture of Methyl (5S,6S)-N'-(6-(3,5-bis (trifluoromethyl)benzyloxymethyl)-2-oxo-5-phenylpiperazin-4-yl-1-iminoethyl)hydrazinocarboxylate To a solution of (5S,6S)-6-(3,5-bis(trifluoromethyl) benzyloxymethyl)-5-phenylpiperazin-2-one hydrochloride (Compound 5) (3 g, 7.3 mmol) in acetonitrile (10 mL) were added diisopropylethylamine (2.5 mL, 14.6 mmol) and methyl N'-(2-chloro-1-iminoethyl)hydrazinocarboxylate (1.8 g, 11.0 mmol). The mixture was stirred at room temperature for 8 hours and the solvent was removed by evaporation from the filtrate under reduced pressure. The residue was dissolved in ether and washed with saturated NH$_4$Cl solution and saturated brine in order. The organic layer was dried over sodium sulfate anhydride. Sodium sulfate was filtered off and the solvent was removed by evaporation from the filtrate under reduced pressure. The residue was purified on a silica gel column chromatograph (CHCl$_3$:MeOH=10:1) to give methyl (5S,6S)-N'-(6-(3,5-bis (trifluoromethyl)benzyloxymethyl)-2-oxo-5-phenylpiperazin-4-yl-1-iminoethyl)hydrazinocarboxylate (3.5 g, 86%) as white crystals.

$^1$H-NMR (DMSO-d$_6$) δ: 2.71 (d, J=13.4 Hz, 1H), 2.85–2.89 (m, 2H), 3.10 (d, J=17.0 Hz, 1H), 3.28–3.34 (m, 1H), 3.45–3.48 (m, 1H), 3.56 (s, 1H), 4.01–4.07 (m, 2H), 4.42 (d, J=12.8 Hz, 1H), 4.52 (d, J=12.8 Hz, 1H), 6.00 (s, 2H), 7.28–7.36 (m, 5H), 7.91 (s, 2H), 7.99 (s, 1H), 8.19 (s, 1H), 9.04 (s, 1H).

(G) Manufacture of (5S,6S)-6-(3,5-bis(trifluoromethyl) benzyloxymethyl)-4-(5-oxo-4,5-dihydro-1H-(1,2,4)triazol-3-ylmethyl)-5-phenylpiperazin-2-one (Compound 12)

A solution of methyl (5S,6S)-N'-(6-(3,5-bis (trifluoromethyl)benzyloxymethyl)-2-oxo-5-phenylpiperazin-4-yl-1-iminoethyl)hydrazinocarboxylate (5.2 g, 9.3 mmol) in DMF (100 mL) was stirred at 140° C. for 2 hours. The reaction mixture was cooled to room temperature, diluted with water (300 mL) and extracted with ethyl acetate (200 L). The organic layer was separated and dried over sodium sulfate anhydride. Sodium sulfate was filtered off and the solvent was removed by evaporation from the filtrate under reduced pressure. The residue was purified on a silica gel column chromatography (CHCl$_3$:MeOH= 10:1) to give (5S,6S)-6-(3,5-bis(trifluoromethyl) benzyloxymethyl)-4-(5-oxo-4,5-dihydro-1H-(1,2,4)triazol-3-ylmethyl)-5-phenylpiperazin-2-one (Compound 12) (2.5 g, 51%) as white crystals.

Mp. 138–140° C. $^1$H-NMR (DMSO-d$_6$) δ: 2.97 (d, J=17.0 Hz, 1H), 3.15 (d, J=17.0 Hz, 1H), 3.20 (brs, 2H), 3.28–3.32

(m, 1H), 3.42–3.45 (m, 1H), 3.99–4.04 (m, 2H), 4.41 (d, J=12.8 Hz, 1H), 4.50 (d, J=12.8 Hz, 1H), 7.28–7.37 (m, 5H), 7.89 (s, 2H), 7.98 (s, 1H), 8.19 (s., 1H), 11.28 (s, 1H), 11.39 (s, 1H) . $[\alpha]_D$=52.3°(c1, MeOH).

(H) Manufacture of Benzyl (5S,6S)-3-(6-(3,5-bis(trifluoromethyl)benzyloxymethyl)-2-oxo-5-phenylpiperazin-4-ylmethyl-5-oxo-4,5-dihydro-(1,2,4)triazol-1-yl)phosphonate A solution of (5S,6S)-6-(3,5-bis(trifluoromethyl)benzyloxymethyl)-4-(5-oxo-4,5-dihydro-1H-(1,2,4)triazol-3-ylmethyl)-5-phenylpiperazin-2-one (Compound 12) (0.74 g, 1.4 mmol) and tetrabenzylpyrophosphate (TBPP) (0.92 g, 1.7 mmol) in THF (20 mL) was cooled in an ice bath and a solution of NaHMDS (0.64 g, 3.5 mmol) in THF (5 mL) was added dropwise thereto. After stirring at room temperature for 2 hours, the reaction was stopped with saturated NaHCO$_3$ aqueous solution. The resulting product was extracted with ether and purified by washing with 0.5 mol/L KHSO$_4$ solution, saturated NaHCO$_3$ solution and brine in order. The organic extract was dried over sodium sulfate anhydride. Sodium sulfate was filtered off and the solvent was removed by evaporation from the filtrate under reduced pressure to give benzyl (5S,6S)-3-(6-(3,5-bis(trifluoromethyl)benzyloxymethyl)-2-oxo-5-phenylpiperazin-4-ylmethyl-5-oxo-4,5-dihydro-(1,2,4)triazol-1-yl)phosphonate (1.11 g, 99%).

$^1$H-NMR (DMSO-d$_6$) δ: 2.99–3.40 (m, 6H), 3.99–4.12 (m, 2H), 4.41–4.51 (m,2H), 5.13–5.23 (m, 4H), 7.27–7.37 (m, 15H), 7.89 (s, 2H), 7.96 (s, 1H), 8.18 (s, 1H).

(I) Manufacture of (5S,6S)-3-(6-(3,5-bis(trifluoromethyl)benzyloxymethyl)-2-oxo-5-phenylpiperazin-4-ylmethyl-5-oxo-4,5-dihydro-(1,2,4)triazol-1-yl)phosphoric acid, bis(N-methyl-D-glucamine) (Compound 42)

A mixture of dibenzyl (5S,6S)-3-(6-(3,5-bis(trifluoromethyl)benzyloxymethyl)-2-oxo-5-phenylpiperazin-4-ylmethyl-5-oxo-4,5-dihydro-(1,2,4)triazol-1-yl)phosphonate (1.11 g, 1.4 mmol), 20% palladium hydroxide on carbon catalyst (0.12 g) and N-methyl-D-glucamine (0.49 g, 25 mmol) in MeOH (25 mL) and water (5 mL) was stirred under a hydrogen atmosphere for 1 hour. The catalyst was filtered off and the filtrate was concentrated under reduced pressure. The residue was crystallized by adding MeOH (8 mL) and isopropanol (40 mL). The crystals obtained by filtration were dissolved in ether (50 mL) and water (50 mL), and centrifuged at 3000 rpm for 15 minutes. The aqueous layer was separated and further centrifuged after adding ether (50 mL). The collected aqueous layer was lyophilized to give (5S,6S)-3-(6-(3,5-bis(trifluoromethyl)benzyloxymethyl)-2-oxo-5-phenylpiperazin-4-ylmethyl-5-oxo-4,5-dihydro-(1,2,4)triazol-1-yl)phosphoric acid, bis(N-methyl-D-glucamine) (Compound 42) (0.9 g, 64%).

$^1$H-NMR (DMSO-d$_6$) δ: 2.68 (brs, 9H), 3.08–3.22 (m, 7H), 3.33–3.47 (m, 6H), 3.62–3.75 (m, 1H), 3.77–3.80 (m, 7H), 4.11–4.20 (m, 5H), 4.47–4.56 (m, 2H), 7.33–7.37 (m, 5H), 7.83 (s, 3H).

(J) Manufacture of tert-butyl (2S,3S)-3-(3,5-bis(trifluoromethyl)benzyloxymethyl)-5-oxo-2-phenylpiperizine-1-carboxylate To a solution of (5S,6S)-6-(3,5-bis(trifluoromethyl)benzyloxymethyl)-5-phenylpiperazin-2-one hydrochloride (Compound 5) (10.0 g, 24.3 mmol) and triethylamine (3.7 mL, 26.7 mmol) in CH$_2$Cl$_2$ was added Boc$_2$O (5.8 g, 26.7 mmol). After stirring overnight at room temperature, the reaction mixture was washed with diluted HCl solution. The organic layer was dried over sodium sulfate anhydride. Sodium sulfate was filtered off and the solvent was removed by evaporation from the filtrate under reduced pressure to give (2S,3S)-3-(3,5-bis(trifluoromethyl)benzyloxymethyl)-5-oxo-2-phenylpiperizine-1-carboxylate 11.6 g (90%).

$^1$H-NMR (DMSO-d$_6$) δ: 1.11–1.37 (br, 9H), 3.17–3.21 (m, 1H), 3.29–3.31 (m, 1H), 3.99–4.19 (br, 3H), 4.58 (ABq, J=12.8 Hz, 2H), 5.01–5.28 (br, 1 H), 7.11 (brs, 2H, 7.27–7.33 (m, 3H), 8.04 (s, 3H), 8.19 (brs, 1H).

(K) Manufacture of tert-butyl (2S,3S)-3-(3,5-bis(trifluoromethyl)benzyloxymethyl)-4-methyl-5-oxo-2-phenylpiperizine-1-carboxylate To a solution of tert-butyl (2S,3S)-3-(3,5-bis(trifluoromethyl)benzyloxymethyl)-5-oxo-2-phenylpiperizine-1-carboxylate (6.6 g, 12.4 mmol) and iodomethane (1.0 mL, 16.1 mmol) in THF (50 mL) was added NaH (0.55 g, 13.6 mmol) at 0° C. After stirring overnight, the reaction was stopped with water (50 mL). The product was extracted with ether, and purified by washing with 0.5 mol/L KHSO$_4$ solution, saturated NaHCO$_3$ solution and saturated brine in order. The organic layer was dried over sodium sulfate anhydride. Sodium sulfate was filtered off and the solvent was removed by evaporation from the filtrate under reduced pressure to give tert-Butyl (2S,3S)-3-(3,5-bis(trifluoromethyl)benzyloxymethyl)-4-methyl-5-oxo-2-phenylpiperizine-1-carboxylate 6.5 g (96%) was obtained.

$^1$H-NMR (DMSO-d$_6$) δ: 0.92–1.43 (br, 9H), 2.83 (s, 3H), 3.45 (s, 2H), 4.06–4.10 (m, 1H), 4.20–4.28 (m, 2H), 4.55 (ABq, J=12.8 Hz, 2H), 5.13 (s, 1H), 7.15–7.16 (m, 2H), 7.24–7.32 (m, 3H), 7.91 (s, 2H), 8.02 (s, 1H).

(L) Manufacture of (5S,6S)-6-(3,5-bis(trifluoromethyl)benzyloxymethyl)-1-methyl-5-phenylpiperazin-2-one hydrochloride (Compound 24)

To a solution of tert-butyl (2S,3S)-3-(3,5-bis(trifluoromethyl)benzyloxymethyl)-4-methyl-5-oxo-2-phenylpiperizine-1-carboxylate (6.5 g, 11.9 mmol) in 1,4-dioxane (100 mL) was added 4 mol/L HCl-1,4-dioxane (15 mL, 59.5 mmol). After stirring at room temperature for 2 hours, the solvent was removed by evaporation under reduced pressure to give (5S,6S)-6-(3,5-bis(trifluoromethyl)benzyloxymethyl)-1-methyl-5-phenylpiperazin-2-one hydrochloride (Compound 24) (5.5 g, 96%).

$^1$H-NMR (DMSO-d$_6$) δ: 2.93 (s, 3H), 2.93–3.17 (m, 1H), 3.57–3.64 (m, 1H), 3.57–3.64 (m, 1H), 3.80–3.84 (m, 1H), 3.95–4.02 (m, 2H), 4.66 (ABq, J=13.2 Hz, 2H), 5.08 (s, 1H), 7.38–7.41 (m, 3H), 7.49–7.50 (m, 2H), 7.99 (s, 2H), 8.04 (s, 1H), 9.40 (brs, 1H), 11.0 (brs, 1H).

(M) Manufacture of methyl (2S,3S)-N'-(2-(3-(3,5-bis(trifluoromethyl)benzyloxymethyl)-4-methyl-5-oxo-2-phenylpiperazin-1-yl)-1-iminoethyl)hydrazinocarboxylate In the same manner as described for the manufacture of methyl (5S,6S)-N'-(6-(3,5-bis(trifluoromethyl)benzyloxymethyl)-2-oxo-5-phenylpiperazin-4-yl-1-iminoethyl)hydrazinocarboxylate, methyl (2S,3S)-N'-(2-(3-(3,5-bis(trifluoromethyl)benzyloxymethyl)-4-methyl-5-oxo-2-phenylpiperazin-1-yl)-1-iminoethyl)hydrazinocarboxylate 6.4 g (97%) was prepared as white crystals from (5S,6S)-6-(3,5-bis(trifluoromethyl)benzyloxymethyl)-1methyl-5-phenylpiperazin-2-one hydrochloride (Compound 24) (5.5 g, 11.4 mmol), acetonitrile (50 mL), diisopropylethylamine (6.0 mL, 34.2 mmol) and methyl N'-(2-chloro-1-iminoethyl)hydrazinocarboxylate (2.8 g, 17.1 mmol).

$^1$H-NMR (DMSO-d$_6$) δ: 2.76 (d, J=14.3 Hz, 1H), 3.09 (s, 3H), 3.21 (d, J=17.3 Hz, 1H), 3.46 (d, J=14.3 Hz, 1H), 3.62 (d, J=17.3 Hz, 1H), 3.68–3.76 (m, 5H), 4.10–4.11 (m, 1H), 4.42 (ABq, J=12.4, 2H), 5.51–5.58 (br, 2H), 7.27–7.36 (m, 6H), 7.56 (s, 2H), 7.77 (s, 1H).

(N) Manufacture of (5S,6S)-6-(3,5-bis(trifluoromethyl) benzyloxymethyl)-1-methyl-4-(5-oxo-4,5-dihydro-1H-(1,2, 4)triazol-3-ylmethyl)-5-phenylpiperazin-2-one (Compound 26)

In the same manner as described for the manufacture of (5S,6S)-6-(3,5-bis(trifluoromethyl)benzyloxymethyl)-4-(5-oxo-4,5-dihydro-1H-(1,2,4)triazol-3-ylmethyl)-5-phenylpiperazin-2-one (Compound 12), (5S,6S)-6-(3,5-bis(trifluoromethyl)benzyloxymethyl)-1-methyl-4-(5-oxo-4,5-dihydro-1H-(1,2,4)triazol-3-ylmethyl)-5-phenylpiperazin-2-one (Compound 26) (4.5 g, 69%) was prepared as white crystals from methyl (2S,3S)-N'-(2-(3-(3,5-bis (trifluoromethyl)benzyloxymethyl)-4-methyl-5-oxo-2-phenylpiperazin-1-yl)-1-imino-ethyl)-hydrazinocarboxylate (6.4 g, 11.1 mmol) and DMF (50 mL).

Mp 108–111° C. $(\alpha)_D$=38.3°(c1, MeOH). $^1$H-NMR (DMSO-d$_6$) δ: 2.51–2.96 (m, 1H), 2.94 (s, 3H), 3.11 (d, J=17.0 Hz, 1H), 3.35 (d, J=17.0 Hz, 1H), 3.57 (d, J=14.2 Hz, 1H), 3.65–3.67 (m, 1H), 3.70–3.71 (m, 1H), 3.77–3.79 (m, 1H), 4.13 (d, J=3.4 Hz, 1H), 4.44 (d, J=13.0 Hz, 1H), 4.53 (d, J=13.0 Hz, 1H), 7.26–7.28 (m, 1H), 7.33–7.36 (m, 2H), 7.45–7.49 (m, 2H), 7.73 (s, 2H), 7.97 (s, 1H), 11.29 (s, 1H), 11.44 (s, 1H).

In place of D-serine, the starting material in the above Example 1, appropriate starting materials corresponding to each objective product were used and subjected to a similar method employed in Example 1 to prepare other compounds than the above mentioned ones. The manufacturing materials or reagents used and the values of properties of the compounds of the present invention which were obtained were measured and given as follows:

Manufacturing Materials

Compound 1: L-serine, 3,5-bis(trifluoromethyl)benzyl bromide, phenylmagnesium bromide, benzyloxycarbonylglycine, di-t-butyldicarbonate, methoxymethylamine hydrochloride, sodium hydride, WSC—HCl, palladium catalyst, hydrogen chloride.

Compound 2: D-phenylglycine, di-t-butyldicarbonate, methoxymethylamine hydrochloride, 3-(3,5-bis (trifluoromethyl)phenyl)propylmagnesium bromide, methanesulfonyl chloride, sodium azide, chloroacetic chloride, WSC—HCl, palladium catalyst, hydrogen chloride.

Compound 3: D-phenylglycine, di-t-butyldicarbonate, methoxymethylamine hydrochloride, 3-(3,5-bis (trifluoromethyl)phenyl)propylmagnesium bromide, methanesulfonyl chloride, sodium azide, chloroacetic chloride, chloroacetonitrile, methylcarbamate, WSC—HCl, palladium catalyst, hydrogen chloride, potassium carbonate, sodium methoxide.

Compound 4: D-phenylglycine, di-t-butyldicarbonate, methoxymethylamine hydrochloride, 3-(3,5-bis (trifluoromethyl)phenyl)propylmagnesium bromide, methanesulfonyl chloride, sodium azide, chloroacetic chloride, chloroacetonitrile, formic hydrazide, WSC—HCl, palladium catalyst, hydrogen chloride, potassium carbonate, sodium methoxide.

Compound 5: D-serine, 3,5-bis(trifluoromethyl)benzyl bromide, phenylmagnesium bromide, benzyloxycarbonylglycine, di-t-butyldicarbonate, methoxymethylamine hydrochloride, sodium hydride, WSC—HCl, palladium catalyst, hydrogen chloride.

Compound 6: D-phenylglycine, di-t-butyldicarbonate, methoxymethylamine hydrochloride, 2-(2-methoxyphenyl) ethylmagnesium bromide, methanesulfonyl chloride, sodium azide, chloroacetic chloride, WSC—HCl, palladium catalyst, hydrogen chloride, potassium carbonate.

Compound 7: D-phenylglycine, di-t-butyldicarbonate, methoxymethylamine hydrochloride, 2-(2-methoxyphenyl) ethylmagnesium bromide, methanesulfonyl chloride, sodium azide, chloroacetic chloride, WSC—HCl, palladium catalyst, hydrogen chloride, potassium carbonate.

Compound 8: D-serine, 3,5-bis(trifluoromethyl)benzyl bromide, benzyloxycarbonylglycine, di-t-butyldicarbonate, methoxymethylamine hydrochloride, sodium hydride, WSC—HCl, palladium catalyst, hydrogen chloride, lithium aluminum hydride.

Compound 9: D-phenylglycine, di-t-butyldicarbonate, methoxymethylamine hydrochloride, 2-phenylethylmagnesium bromide, methanesulfonyl chloride, sodium azide, chloroacetic chloride, WSC—HCl, palladium catalyst, hydrogen chloride, potassium carbonate, lithium aluminum hydride.

Compound 10: D-phenylglycine, di-t-butyldicarbonate, methoxymethylamine hydrochloride, 2-(2-methoxyphenyl) ethylmagnesium bromide, methanesulfonyl chloride, sodium azide, chloroacetic chloride, WSC—HCl, palladium catalyst, hydrogen chloride, potassium carbonate, lithium aluminum hydride.

Compound 11: D-serine, 2-methoxyphenol, phenylmagnesium bromide, benzyloxycarbonylglycine, di-t-butyldicarbonate, methoxymethylamine hydrochloride, WSC—HCl, palladium catalyst, hydrogen chloride, potassium carbonate, triphenylphosphine, diethylazacarbodiimide.

Compound 12: D-serine, 3,5-bis(trifluoromethyl)benzyl bromide, phenylmagnesium bromide, benzyloxycarbonylglycine, di-t-butyldicarbonate, methoxymethylamine hydrochloride, chloroacetonitrile, methylcarbamate, sodium hydride, WSC—HCl, palladium catalyst, hydrogen chloride, sodium methoxide, diisopropylethylamine.

Compound 13: serine, N-(3,5-bis(trifluoromethyl) benzyl)-N-methylamine, phenylmagnesium bromide, benzyloxycarbonylglycine, di-t-butyldicarbonate, methoxymethylamine hydrochloride, methyl iodide, sodium hydride, WSC—HCl, palladium catalyst, hydrogen chloride, tetrapropylammonium perruthenate, N-methylmorpholine-N-oxide.

Compound 14: D-serine, 3,5-bis(trifluoromethyl)benzyl bromide, phenylmagnesium bromide, benzyloxycarbonylglycine, di-t-butyldicarbonate, methoxymethylamine hydrochloride, diphenyl cyanocarbonimidate, hydrazine, sodium hydride, WSC—HCl, palladium catalyst, hydrogen chloride, triethylamine.

Compound 15: D-serine, 3,5-bis(trifluoromethyl)benzyl bromide, phenylmagnesium bromide, benzyloxycarbonylglycine, di-t-butyldicarbonate, methoxymethylamine hydrochloride, pyrrolidineacetic acid hydrochloride, sodium hydride, WSC—HCl, palladium catalyst, hydrogen chloride, triethylamine.

Compound 16: D-serine, 3,5-bis(trifluoromethyl)benzyl bromide, phenylmagnesium bromide, benzyloxycarbonylglycine, di-t-butyldicarbonate, methoxymethylamine hydrochloride, chloroacetamide, sodium hydride, WSC—HCl, palladium catalyst, hydrogen chloride, triethylamine.

Compound 17: D-serine, 3,5-bis(trifluoromethyl)benzyl bromide, phenylmagnesium bromide, benzyloxycarbonylglycine, di-t-butyldicarbonate, methoxymethylamine hydrochloride, chloroacetonitrile, sodium hydride, WSC—HCl, palladium catalyst, hydrogen chloride, triethylamine.

Compound 18: D-serine, 3,5-bis(trifluoromethyl)benzyl bromide, phenylmagnesium bromide, benzyloxycarbonylglycine, di-t-butyldicarbonate, methoxymethylamine hydrochloride, cyanogens bromide, sodium hydride, WSC—HCl, palladium catalyst, hydrogen chloride, triethylamine.

Compound 19: D-serine, 3,5-bis(trifluoromethyl)benzyl bromide, phenylmagnesium bromide, benzyloxycarbonylglycine, di-t-butyldicarbonate, methoxymethylamine hydrochloride, cyanogens bromide, sodium azide, sodium hydride, WSC—HCl, palladium catalyst, hydrogen chloride, triethylamine, ammonium chloride.

Compound 20: D-serine, 3,5-bis(trifluoromethyl)benzyl bromide, phenylmagnesium bromide, benzyloxycarbonylglycine, di-t-butyldicarbonate, methoxymethylamine hydrochloride, dimethyl aminoacetate hydrochloride, sodium hydride, WSC—HCl, palladium catalyst, hydrogen chloride, triethylamine.

Compound 21: D-serine, 3,5-bis(trifluoromethyl)benzyl bromide, phenylmagnesium bromide, benzyloxycarbonylglycine, di-t-butyldicarbonate, methoxymethylamine hydrochloride, chloroacetonitrile, formic hydrazide, sodium hydride, WSC—HCl, palladium catalyst, hydrogen chloride, triethylamine.

Compound 22: D-serine, 3,5-bis(trifluoromethyl)benzyl bromide, phenylmagnesium bromide, benzyloxycarbonylglycine, di-t-butyldicarbonate, methoxymethylamine hydrochloride, 4-pyridylacetic acid hydrochloride, sodium hydride, WSC—HCl, palladium catalyst, hydrogen chloride, triethylamine.

Compound 23: D-serine, 3,5-bis(trifluoromethyl)benzyl bromide, phenylmagnesium bromide, benzyloxycarbonylglycine, di-t-butyldicarbonate, methoxymethylamine hydrochloride, methanesulfonyl chloride, sodium hydride, WSC—HCl, palladium catalyst, hydrogen chloride, triethylamine.

Compound 24: D-serine, 3,5-bis(trifluoromethyl)benzyl bromide, benzyloxycarbonylglycine, di-t-butyldicarbonate, methoxymethylamine hydrochloride, methyl iodide, sodium hydride, WSC—HCl, palladium catalyst, hydrogen chloride, triethylamine.

Compound 25: D-serine, 3,5-bis(trifluoromethyl)benzyl bromide, phenylmagnesium bromide, benzyloxycarbonylglycine, di-t-butyldicarbonate, methoxymethylamine hydrochloride, 1,4-dichloro-2-butyne, sodium azide, dimethylamine, sodium hydride, WSC—HCl, palladium catalyst, hydrogen chloride, triethylamine.

Compound 26: D-serine, 3,5-bis(trifluoromethyl)benzyl bromide, phenylmagnesium bromide, benzyloxycarbonylglycine, di-t-butyldicarbonate, methoxymethylamine hydrochloride, methyl iodide, chloroacetonitrile, methylcarbamate, sodium hydride, WSC—HCl, palladium catalyst, hydrogen chloride, diisopropylethylamine, sodium methoxide.

Compound 27: L-serine, 3,5-bis(trifluoromethyl)benzyl bromide, phenylmagnesium bromide, benzyloxycarbonylglycine, di-t-butyldicarbonate, methoxymethylamine hydrochloride, chloroacetonitrile, methylcarbamate, sodium hydride, WSC—HCl, palladium catalyst, hydrogen chloride, triethylamine.

Compound 28: serine, N-(3,5-bis(trifluoromethyl)benzyl)-N-methylamine, phenylmagnesium bromide, benzyloxycarbonylglycine, di-t-butyldicarbonate, methoxymethylamine hydrochloride, sodium hydride, WSC—HCl, palladium catalyst, hydrogen chloride, tetrapropylammonium perruthenate, N-methylmorpholine-N-oxide.

Compound 29: L-serine, 3,5-bis(trifluoromethyl)benzyl bromide, phenylmagnesium bromide, benzyloxycarbonylglycine, di-t-butyldicarbonate, methoxymethylamine hydrochloride, benzyl bromide, sodium hydride, WSC—HCl, palladium catalyst, hydrogen chloride, triethylamine.

Compound 30: D-serine, 3,5-bis(trifluoromethyl)benzyl bromide, 4-fluorophenylmagnesium bromide, benzyloxycarbonylglycine, di-t-butyldicarbonate, methoxymethylamine hydrochloride, sodium hydride, WSC—HCl, palladium catalyst, hydrogen chloride, triethylamine.

Compound 31: L-serine, 3,5-bis(trifluoromethyl)benzyl bromide, phenylmagnesium bromide, benzyloxycarbonylglycine, di-t-butyldicarbonate, methoxymethylamine hydrochloride, benzyl bromide, sodium hydride, WSC—HCl, palladium catalyst, hydrogen chloride, triethylamine, lithium aluminum hydride.

Compound 32: D-serine, 3,5-bis(trifluoromethyl)benzyl bromide, 4-fluorophenylmagnesium bromide, benzyloxycarbonylglycine, di-t-butyldicarbonate, methoxymethylamine hydrochloride, chloroacetonitrile, methylcarbamate, sodium hydride, WSC—HCl, palladium catalyst, hydrogen chloride, diisopropylethylamine, sodium methoxide.

Compound 33: D-serine, 3,5-bis(trifluoromethyl)benzyl bromide, 4-methylphenylmagnesium bromide, benzyloxycarbonylglycine, di-t-butyldicarbonate, methoxymethylamine hydrochloride, sodium hydride, WSC—HCl, palladium catalyst, hydrogen chloride, triethylamine.

Compound 34: D-serine, 3,5-bis(trifluoromethyl)benzyl bromide, 4-methylphenylmagnesium bromide, benzyloxycarbonylglycine, di-t-butyldicarbonate, methoxymethylamine hydrochloride, chloroacetonitrile, methylcarbamate, sodium hydride, WSC—HCl, palladium catalyst, hydrogen chloride, diisopropylethylamine, sodium methoxide.

Compound 35: serine, 3,5-bis(trifluoromethyl)benzyl bromide, phenylmagnesium bromide, benzyloxycarbonylglycine, di-t-butyldicarbonate, methoxymethylamine hydrochloride, benzyl bromide, chloroacetonitrile, methylcarbamate, sodium hydride, WSC—HCl, palladium catalyst, hydrogen chloride, diisopropylethylamine, sodium methoxide, lithium aluminum hydride.

Compound 36: D-serine, 3,5-bis(trifluoromethyl)benzyl bromide, 4-fluorophenylmagnesium bromide, benzyloxycarbonylglycine, di-t-butyldicarbonate, methoxymethylamine hydrochloride, methyl iodide, sodium hydride, WSC—HCl, palladium catalyst, hydrogen chloride.

Compound 37: D-serine, 3,5-bis(trifluoromethyl)benzyl bromide, 4-fluorophenylmagnesium bromide, benzyloxycarbonylglycine, di-t-butyldicarbonate, methoxymethylamine hydrochloride, methyl iodide, sodium hydride, WSC—HCl, palladium catalyst, hydrogen chloride.

Compound 38: D-serine, 3,5-bis(trifluoromethyl)benzyl bromide, 4-fluorophenylmagnesium bromide, benzyloxycarbonylglycine, di-t-butyldicarbonate, methoxymethylamine hydrochloride, methyl iodide, chloroacetonitrile, methylcarbamate, sodium hydride, WSC—HCl, palladium catalyst, hydrogen chloride, diisopropylethylamine, sodium methoxide.

Compound 39: D-serine, 3,5-bis(trifluoromethyl)benzyl bromide, 4-fluorophenylmagnesium bromide, benzyloxycarbonylglycine, di-t-butyldicarbonate, methoxymethylamine hydrochloride, 1,4-dichloro-2-butyne, sodium azide, dimethylamine, sodium hydride, WSC—HCl, palladium catalyst, hydrogen chloride, diisopropylethylamine.

Compound 40: D-serine, 3,5-bis(trifluoromethyl)benzyl bromide, 4-fluorophenylmagnesium bromide, benzyloxycarbonylglycine, di-t-butyldicarbonate, methoxymethylamine hydrochloride, chloroacetonitrile, methylcarbamate, sodium hydride, WSC—HCl, palladium catalyst, hydrogen chloride, diisopropylethylamine, sodium methoxide.

Compound 41: D-serine, 3,5-bis(trifluoromethyl)benzyl bromide, 4-fluorophenylmagnesium bromide, benzyloxycarbonylglycine, di-t-butyldicarbonate, methoxymethylamine hydrochloride, methyl iodide, 1,4-dichloro-2-butyne, sodium azide, dimethylamine, sodium hydride, WSC—HCl, palladium catalyst, hydrogen chloride, diisopropylethylamine.

Compound 42: D-serine, 3,5-bis(trifluoromethyl)benzyl bromide, phenylmagnesium bromide, benzyloxycarbonylglycine, di-t-butyldicarbonate, methoxymethylamine hydrochloride, chloroacetonitrile, methylcarbamate, tetrabenzyl pyrophosphate, N-methyl-D-glucan, sodium hydride, WSC—HCl, palladium catalyst, hydrogen chloride, diisopropylethylamine, sodium methoxide.

Compound 43: D-serine, 3,5-bis(trifluoromethyl)benzyl bromide, 4-methylphenylmagnesium bromide, benzyloxycarbonylglycine, di-t-butyldicarbonate, methoxymethylamine hydrochloride, methyl iodide, chloroacetonitrile, methylcarbamate, sodium hydride, WSC—HCl, palladium catalyst, hydrogen chloride, diisopropylethylamine, sodium methoxide.

Compound 44: D-serine, 3,5-bis(trifluoromethyl)benzyl bromide, 4-methylphenylmagnesium bromide, benzyloxycarbonylglycine, di-t-butyldicarbonate, methoxymethylamine hydrochloride, ethyl iodide, chloroacetonitrile, methylcarbamate, sodium hydride, WSC—HCl, palladium catalyst, hydrogen chloride, diisopropylethylamine, sodium methoxide.

Compound 45: D-serine, 3,5-bis(trifluoromethyl)benzyl bromide, 4-fluorophenylmagnesium bromide, benzyloxycarbonylglycine, di-t-butyldicarbonate, methoxymethylamine hydrochloride, ethyl iodide, chloroacetonitrile, methylcarbamate, sodium hydride, WSC—HCl, palladium catalyst, hydrogen chloride, diisopropylethylamine, sodium methoxide.

Compound 46: D-serine, 3,5-bis(trifluoromethyl)benzyl bromide, 4-fluorophenylmagnesium bromide, benzyloxycarbonylglycine, di-t-butyldicarbonate, methoxymethylamine hydrochloride, propyl iodide, chloroacetonitrile, methylcarbamate, sodium hydride, WSC—HCl, palladium catalyst, hydrogen chloride, diisopropylethylamine, sodium methoxide.

Compound 47: D-serine, 3,5-bis(trifluoromethyl)benzyl bromide, 4-isopropylphenylmagnesium bromide, benzyloxycarbonylglycine, di-t-butyldicarbonate, methoxymethylamine hydrochloride, methyl iodide, chloroacetonitrile, methylcarbamate, sodium hydride, WSC—HCl, palladium catalyst, hydrogen chloride, diisopropylethylamine, sodium methoxide.

Compound 48: D-serine, 3,5-bis(trifluoromethyl)benzyl bromide, 4-methoxyphenylmagnesium bromide, benzyloxycarbonylglycine, di-t-butyldicarbonate, methoxymethylamine hydrochloride, methyl iodide, chloroacetonitrile, methylcarbamate, sodium hydride, WSC—HCl, palladium catalyst, hydrogen chloride, diisopropylethylamine, sodium methoxide.

Compound 49: D-serine, 3,5-bis(trifluoromethyl)benzyl bromide, phenylmagnesium bromide, benzyloxycarbonylglycine, di-t-butyldicarbonate, methoxymethylamine hydrochloride, ethyl iodide, chloroacetonitrile, methylcarbamate, sodium hydride, WSC—HCl, palladium catalyst, hydrogen chloride, diisopropylethylamine, sodium methoxide.

Compound 50: D-serine, 3,5-bis(trifluoromethyl)benzyl bromide, 3-methylphenylmagnesium bromide, benzyloxycarbonylglycine, di-t-butyldicarbonate, methoxymethylamine hydrochloride, methyl iodide, chloroacetonitrile, methylcarbamate, sodium hydride, WSC—HCl, palladium catalyst, hydrogen chloride, diisopropylethylamine, sodium methoxide.

Compound 51: D-serine, 3,5-bis(trifluoromethyl)benzyl bromide, 4-ethylphenylmagnesium bromide, benzyloxycarbonylglycine, di-t-butyldicarbonate, methoxymethylamine hydrochloride, methyl iodide, chloroacetonitrile, methylcarbamate, sodium hydride, WSC—HCl, palladium catalyst, hydrogen chloride, diisopropylethylamine, sodium methoxide.

Compound 52: D-serine, 3,5-bis(trifluoromethyl)benzyl bromide, 4-methoxyphenylmagnesium bromide, benzyloxycarbonylglycine, di-t-butyldicarbonate, methoxymethylamine hydrochloride, ethyl iodide, chloroacetonitrile, methylcarbamate, sodium hydride, WSC—HCl, palladium catalyst, hydrogen chloride, diisopropylethylamine, sodium methoxide.

Values of Properties

Compound 1: $^1$H-NMR (DMSO-$d_6$) δ: 3.28–3.41 (m, 2H), 3.81 (ABq, J=16.7 Hz, 2H), 3.95–3.99 (m, 1H), 4.57 (s, 2H), 5.01 (s, 1H), 7.35–7.41 (m, 3H), 7.48–7.49 (m, 2H), 7.97 (s, 2H), 8.02 (s, 1H), 8.80 (d, J=3.8 Hz, 1H), 9.76 (brs, 1H), 10.76 (brs, 1H).

Compound 2: $^1$H-NMR (DMSO-$d_6$) δ: 1.37–1.41 (m, 1H), 1.62–1.65 (m, 1H), 2.43–2.50 (m, 1H), 2.60–2.66 (m, 1H), 3.68 (d, J=16.4 Hz, 1H), 3.91 (d, J=16.4 Hz, 1H), 4.06 (d, J=10.4 Hz, 1H), 4.53 (brs, 1H), 7.00 (d, J=7.2 Hz, 2H), 7.12–7.23 (m, 3H), 7.47–7.51 (m, 3H), 7.65–7.67 (m, 2H), 8.64 (s, 1H), 9.99 (s, 1H), 11.02 (s, 1H).

Compound 3: $^1$H-NMR (DMSO-$d_6$) δ: 1.16–1.19 (m, 1H), 1.45–1.49 (m, 1H), 2.42–2.50 (m, 1H), 2.61–2.65 (m, 1H), 2.94 (d, J=14.2 Hz, 1H), 3.02 (d, J=16.6 Hz, 1H), 3.08 (d, J=16.6 Hz, 1H), 3.22 (d, J=14.2 Hz, 1H), 3.47–3.49 (m, 1H), 4.03 (d, J=7.1 Hz, 1H), 7.03 (d, J=7.3 Hz, 1H), 7.11–7.14 (m, 1H), 7.19–7.22 (m, 2H), 7.33–7.42 (m, 5H), 8.13 (s, 1H), 11.24 (s, 1H), 11.30 (s, 1H).

Compound 4: $^1$H-NMR (DMSO-$d_6$) δ: 1.39–1.42 (m, 1H), 1.61–1.63 (m, 1H), 2.40–2.43 (m, 1H), 2.50–2.63 (m, 1H), 3.10–3.27 (m, 3H), 3.34–3.37 (m, 1H), 3.48–3.53 (m, 2H), 3.63–3.65 (m, 2H), 7.02 (brs, 2H), 7.12–7.22 (m, 3H), 7.34–7.43 (m, 5H), 8.04–8.13 (m, 1H), 13.79 (d, J=32.1 Hz, 1H).

Compound 6: $^1$H-NMR (DMSO-$d_6$) δ: 1.37–1.40 (m, 1H), 1.56–1.59 (m, 1H), 2.38–2.41 (m, 1H), 2,65–2.68 (m, 1H), 3.57–3.66 (m, 4H), 3.92 (d, J=16.5 Hz, 1H), 4.05–4.08 (m, 1H), 4.51–4.53 (m, 1H), 6.79–6.85 (m, 2H), 7.00–7.02 (m, 1H), 7.11–7.13 (m, 1H), 7.47–7.50 (m, 3H), 7.65–7.66 (m, 2H), 8.59 (s, 1H), 10.02 (s, 1H), 11.24 (s, 1H).

Compound 7: $^1$H-NMR (DMSO-$d_6$) δ: 1.35–1.38 (m, 1H), 1.54–1.59 (m, 1H), 2.40–2.43 (m, 1H), 2,65–2.71 (m, 1H), 3.55–3.67 (m, 4H), 3.89 (d, J=15.8 Hz, 1H), 4.01–4.08 (m, 1H), 4.51–4.55 (m, 1H), 6.79–6.85 (m, 2H), 6.89–7.03 (m, 1H), 7.11–7.15 (m, 1H), 7.49–7.50 (m, 3H), 7.63–7.66 (m, 2H), 8.57 (s, 1H), 10.20 (s, 1H), 11.44 (s, 1H).

Compound 8: $^1$H-NMR (DMSO-$d_6$) δ: 3.40–3.59 (m, 5H), 4.14–4.18 (m, 1H), 4.30–4.31 (m, 1H), 4.60 (s, 2H), 5.03 (s, 1H), 7.39–7.52 (m, 5H), 8.00 (s, 3H), 10.70 (brs, 4H).

Compound 9: $^1$H-NMR (DMSO-$d_6$) δ: 1.55–1.58 (m, 1H), 1.78–1.81 (m, 1H), 2.37–2.42 (m, 1H), 2.60–2.65 (m, 1H), 3.55–3.58 (m, 3H), 3.72–3.73 (m, 1H), 3.84–3.87 (m, 1H), 4.57 (d, J=11.1 Hz, 1H), 6.94 (d, J=7.5 Hz, 2H), 7.13–7.23 (m, 3H), 7.46–7.49 (m, 3H), 7.68–7.70 (m, 2H), 10.26 (brs, 4H).

Compound 10: $^{1}$H-NMR (DMSO-d$_{6}$) δ: 1.53–1.54 (m, 1H), 1.75–1.79 (m, 1H), 2.37–2.40 (m, 1H), 2.55–2.60 (m, 1H), 3.55–3.58 (m, 3H), 3.59 (s, 3H), 3.70–3.71 (m, 1H), 3.84–3.87 (m, 1H), 4.54 (d, J=11.5 Hz, 1H), 6.91 (d, J=7.1 Hz, 2H), 7.13–7.23 (m, 2H), 7.51–7.56 (m, 3H), 7.68–7.75 (m, 2H), 10.29 (brs, 4H).

Compound 11: $^{1}$H-NMR (DMSO-d$_{6}$) δ: 3.78 (s, 3H), 3.80–3.90 (m, 2H), 3.95–4.05 (m, 2H), 4.15–4.16 (m, 1H), 5.13 (s, 1H), 6.82–7.01 (m, 4H), 7.40–7.53 (m, 5H), 8.81 (d, J=3.5 Hz, 1H), 9.51 (s, 1H), 10.99 (s, 1H).

Compound 13: $^{1}$H-NMR (DMSO-d$_{6}$) δ: 0.97 (s, 9H), 2.73 (s, 3H), 2.99–3.03 (s, 3H), 4.18 (d, J=16.2 Hz, 1H), 4.43–4.74 (m, 3H), 7.19–7.32 (m, 5H), 7.40–7.75 (s, 2H), 7.91–8.00 (s, 1H).

Compound 14: $^{1}$H-NMR (DMSO-d$_{6}$) δ: 3.25–3.28 (m, 2H), 3.70 (d, J=18.9 Hz, 1H), 4.01 (d, J=17.5 Hz, 1H), 4.20–4.21 (m, 1H), 4.56 (ABq, J=12.6 Hz, 2H), 5.16 (d, J=4.2 Hz, 2H), 5.76 (brs, 2H), 7.18–7.19 (m, 2H), 7.24–7.29 (m, 3H), 8.03 (s, 3H), 8.13 (s, 1H), 10.93 (brs, 1H).

Compound 15: $^{1}$H-NMR (DMSO-d$_{6}$) δ: 1.84–1.98 (m, 4H), 3.01–3.14 (m, 2H), 3.26–3.57 (m, 4H), 4.14–4.63 (m, 7H), 5.48 (d, J=3.6 Hz, 1H), 7.18–7.20 (m, 2H), 7.30–7.39 (m, 3H), 8.05–8.07 (m, 3H), 8.40 (s, 1H), 10.04 (brs, 1H).

Compound 16: $^{1}$H-NMR (DMSO-d$_{6}$) δ: 3.26–3.29 (m, 2H), 3.36–3.41 (m, 1H), 3.48–3.51 (m, 1H), 3.62 (ABq, J=16.0 Hz, 2H), 4.30 (brs, 1H), 4.50 (ABq, J=12.7 Hz, 2H), 4.76 (brs, 1H), 7.33–7.34 (m, 2H), 7.40–7.43 (m, 3H), 7.47 (s, 1H), 7.71 (s, 1H), 7.93 (s, 2H), 8.01 (s, 1H), 8.61 (s, 1H).

Compound 17: $^{1}$H-NMR (DMSO-d$_{6}$) δ: 3.34–3.61 (m, 6H), 3.71–3.74 (m, 1H), 4.03 (d, J=4.3 Hz, 1H), 4.48 (ABq, J=12.8 Hz, 2H), 7.32–7.39 (m, 5H), 7.90 (s, 2H), 7.98 (s, 1H), 8.35 (s, 1H).

Compound 18: $^{1}$H-NMR (DMSO-d$_{6}$) δ: 3.26–3.29 (m, 1H), 3.36–3.39 (m, 1H), 4.04–4.08 (m, 1H), 4.12 (ABq, J=16.0 Hz, 2H), 4.55 (s, 2H), 4.91 (d, J=4.1 Hz, 1H), 7.33–7.42 (m, 5H), 7.98 (s, 2H), 8.01 (s, 1H), 8.49 (d, J=2.0 Hz, 1H).

Compound 19: $^{1}$H-NMR (DMSO-d$_{6}$) δ: 3.24–3.27 (m, 2H), 4.16 (ABq, J=16.5 Hz, 2H), 4.36–4.38 (m, 1H), 4.58–4.64 (m, 2H), 5.19 (d, J=3.8 Hz, 1H), 7.22–7.33 (m, 5H), 8.06 (s, 3H), 8.35 (s, 1H), 15.07 (brs, 1H).

Compound 20: $^{1}$H-NMR (DMSO-d$_{6}$) δ: 2.09 (s, 2H), 2.12 (s, 4H), 2.92–3.40 (m, 4H), 4.06–4.46 (m, 3H), 4.60–4.63 (m, 2H), 5.53 (ABq, J=3.5 Hz, 2H), 7.14 (d, J=6.8 Hz, 2H), 7.27–7.38 (m, 3H), 8.04–8.07 (m, 3H), 8.23 (s, 1H).

Compound 21: $^{1}$H-NMR (DMSO-d$_{6}$) δ: 2.96–3.08 (m, 2H), 3.19–3.25 (m, 1H), 3.31–3.36 (m, 2H), 3.41–3.44 (m, 1H), 3.52 (t, J=9.2 Hz, 1H), 4.12–4.23(m, 2H), 4.46 (d, J=12.6 Hz, 1H), 4.56 (d, J=12.6 Hz, 1H), 7.30–7.38 (m, 5H), 7.83–7.84 (m, 3H), 7.92–8.32 (s, 1H).

Compound 22: $^{1}$H-NMR (DMSO-d$_{6}$) δ: 3.17–3.45 (m, 3H), 3.82 (ABq, J=3.4 Hz, 2H), 4.13–4.15 (m, 1H), 4.35 (ABq, J=16.7 Hz, 2H), 4.60–4.62 (m, 2H), 5.34–5.52 (m, 1H), 6.95–7.38 (m, 7H), 8.04–8.08 (m, 3H), 8.30–8.45 (m, 3H).

Compound 23: $^{1}$H-NMR (DMSO-d$_{6}$) δ: 2.78 (s, 3H), 3.12–3.15 (m, 1H), 3.31–3.37 (m, 1H), 4.02 (ABq, J=16.3 Hz, 2H), 4.19–4.22 (m, 1H), 4.55 (ABq, J=12.6 Hz, 2H), 5.04 (d, J=4.1 Hz, 1H), 7.20–7.21 (m, 2H), 7.32–7.38 (m, 3H), 8.02 (s, 3H), 8.37 (s, 1H).

Compound 25: $^{1}$H-NMR (DMSO-d$_{6}$) δ: 2.25 (s, 6H), 3.30–3.59 (m, 8H), 3.99 (d, J=4.7 Hz, 1H), 4.13–4.14 (m, 1H), 4.46 (ABq, J=12.4 Hz, 2H), 6.71 (s, 1H), 7.27 (m, 1H), 7.32–7.40 (m, 5H), 7.67 (s, 2H), 7.78 (s, 1H).

Compound 27: Mp. 138–140° C. $^{1}$H-NMR (DMSO-d$_{6}$) δ: 2.97 (d, J=17.0 Hz, 1H), 3.15 (d, J=17.0 Hz, 1H), 3.20 (brs, 2H), 3.28–3.32 (m, 1H), 3.42–3.45 (m, 1H), 3.99–4.04 (m, 2H), 4.41 (d, J=12.8 Hz, 1H), 4.50 (d, J=12.8 Hz, 1H), 7.28–7.37 (m, 5H), 7.89 (s, 2H), 7.98 (s, 1H), 8.19 (s., 1H), 11.28 (s, 1H), 11.39 (s, 1H). (α)$_{D}$=−52.3° (c1, MeOH).

Compound 28: $^{1}$H-NMR (DMSO-d$_{6}$) δ: 2.68–2.84 (s, 3H), 3.32 (s, 2H), 4.40–4.74 (s, 2H), 7.26–7.64 (m, 6H), 7.96–8.09 (s, 2H), 8.26 (s, 1H), 12.25 (brs, 1H).

Compound 29: $^{1}$H-NMR (DMSO-d$_{6}$) δ: 3.00 (ABq, J=17.1 Hz, 2H), 3.28–3.33 (m, 2H), 3.42–4.45 (m, 2H), 4.00–4.02 (m, 1H), 4.05–4.06 (m, 1H), 4.46 (ABq, J=12.8 Hz, 2H), 7.17–7.37 (m, 10H), 7.89 (s, 2H), 7.97 (s, 1H), 8.16 (s, 1H).

Compound 30: $^{1}$H-NMR (DMSO-d$_{6}$) δ: 2.98–3.00 (br, 1H), 3.30–4.42 (m, 4H), 3.68–3.72 (m, 1H), 4.24 (s, 1H), 4.41 (ABq, J=13.0 Hz, 2H), 7.07–7.10 (m, 2H), 7.39–7.42 (m, 2H), 7.81 (s, 2H), 7.96 (s, 1H), 8.11 (d, J=3.8 Hz, 1H).

Compound 31: $^{1}$H-NMR (DMSO-d$_{6}$) δ: 1.46–1.48 (br, 1H), 2.02–2.06 (m, 1H), 2.81–3.07 (m, 3H), 3.29–3.31 (m, 1H), 3.57–3.58 (m, 1H), 3.79–3.86 (m, 2H), 4.05–4.09 (m, 1H), 4.29–4.50 (m, 3H), 7.24–7.40 (m, 10H), 7.82 (s, 2H), 7.96 (s, 1H).

Compound 32: Mp 129–132° C. (α)$_{D}$=50.1°(c1, MeOH). $^{1}$H-NMR (DMSO-d$_{6}$) δ:2.97 (d, J=17.0 Hz, 1H), 3.15 (d, J=17.0 Hz, 1H), 3.20 (bs, 2H), 3.28–3.32 (m, 1H), 3.39–3.42 (m, 1H), 3.97–3.98 (m, 1H), 4.05–4.06 (m, 1H), 4.41 (d, J=12.8 Hz, 1H), 4.50 (d, J=12.8 Hz, 1H), 7.15–7.19 (m, 2H), 7.31–7.34 (m, 2H), 7.87 (s, 2H), 7.98 (s, 1H), 8.31 (s., 1H), 11.28 (s, 1H), 11.38 (s, 1H).

Compound 33: $^{1}$H-NMR (DMSO-d$_{6}$) δ: 2.22 (s, 3H), 2.92–3.44 (m, 4H), 3.65–3.68 (m, 1H), 4.19–4.20 (m, 1H), 4.42 (s, 2H), 7.08 (d, J=7.9 Hz, 2H), 7.23 (d, J=7.9 Hz, 2H), 7.86 (s, 2H), 7.96 (s, 1H), 8.11 (d, J=3.8 Hz, 1H).

Compound 34: $^{1}$H-NMR (DMSO-d$_{6}$) δ: 2.99 (ABq, J=17.0 Hz, 2H), 3.17–3.18 (m, 2H), 3.27–3.28 (m, 2H), 3.40–3.43 (m, 1H), 3.98 (s, 2H), 4.46 (ABq, J=12.8 Hz, 2H), 7.15 (4, 4H), 7.89 (s, 2H), 7.97 (s, 1H), 8.14 (s, 1H), 11.26 (s, 1H), 11.35 (s, 1H).

Compound 35: $^{1}$H-NMR (DMSO-d$_{6}$) δ: 2.61–2.64 (m, 1H), 3.00 (d, J=12.6 Hz, 1H), 3.20–3.22 (m, 2H), 3.21 (ABq, J=14,5 Hz, 2H), 3.38–3.45 (m, 2H), 3.81–3.83 (m, 1H), 4.01–4.03 (m, 1H), 4.59 (ABq, J=12.7 Hz, 2H), 7.32–7.42 (m, 5H), 7.95 (s, 2H), 8.00 (s, 1H), 8.82 (brs, 1H), 9.98 (brs, 1H), 11.34 (s, 1H), 11.49 (s, 1H).

Compound 36: $^{1}$H-NMR (DMSO-d$_{6}$) δ: 1.63 (d, J=6.8 Hz, 3H), 2.90 (s, 3H), 3.43 (ABq, J=11.2 Hz, 2H), 3.91–3.95 (m, 1H), 3.15–3.18 (m, 1H), 4.65 (ABq, J=13.0 Hz, 2H), 5.27–5.31 (m, 1H), 7.24–7.27 (m, 2H), 7.57–7.58 (m, 2H), 7.95 (s, 2H), 8.05 (s, 1H), 9.68 (brs, 1H), 10.33 (brs, 1H).

Compound 37: $^{1}$H-NMR (DMSO-d$_{6}$) δ: 2.92 (s, 3H), 3.16–3.18 (m, 1H), 3.63–3.64 (m, 1H), 3.80–3.83 (m, 1H), 3.95–4.01 (m, 2H), 4.65 (ABq, J=13.5 Hz, 2H), 5.09–5.13 (m, 1H), 7.24–7.27 (m, 2H), 7.54–7.55 (m, 2H), 7.95 (s, 2H), 8.05 (s, 1H), 9.33 (brs, 1H), 10.91 (brs, 1H).

Compound 38: Mp 212–213° C. $^{1}$H-NMR (DMSO-d$_{6}$) δ: 2.95–2.97 (m, 4H), 3.12 (d, J=17.0 Hz, 1H), 3.31–3.36 (m, 1H), 3.53 (d, J=23.7 Hz, 1H), 3.59–3.62 (m, 1H), 3.67–3.69 (m, 1H), 3.78–3.82 (m, 1H), 4.15 (d, J=3.3 Hz, 1H), 4.44 (d, J=13.0 Hz, 1H), 4.54 (d, J=13.0 Hz, 1H), 7.12–7.15 (m, 2H), 7.50–7.53 (m, 2H), 7.72 (s, 2H), 7.97 (s, 1H), 11.28 (s, 1H), 11.42 (s, 1H).

Compound 39: Mp 213–216° C. $^{1}$H-NMR (DMSO-d$_{6}$) δ: 2.76 (s, 3H), 2.77 (s, 3H), 3.17–3.25 (m, 2H), 3.36–3.46 (m, 3H), 3.69–3.72 (m, 1H), 4.04–4.08 (m, 1H), 4.25–4.26 (m, 1H), 4.43 (d, J=12.7 Hz, 3H), 4.54 (d, J=12.7 Hz, 1H), 4.82–5.79 (br, 2H), 7.21–7.27 (m, 2H), 7.33–7.53 (m, 2H), 7.89 (s, 2H), 7.99 (s, 1H), 8.15–8.46 (br, 1H), 10.69 (brs, 1H).

Compound 40: Mp. 138–140° C. $^1$H-NMR (DMSO-d$_6$) δ: 2.97 (d, J=17.0 Hz, 1H), 3.15 (d, J=17.0 Hz, 1H), 3.20 (brs, 2H), 3.28–3.32 (m, 1H), 3.42–3.45 (m, 1H), 3.99–4.04 (m, 2H), 4.41 (d, J=12.8 Hz, 1H), 4.50 (d, J=12.8 Hz, 1H), 7.28–7.37 (m, 5H), 7.89 (s, 2H), 7.98 (s, 1H), 8.19 (s., 1H), 11.28 (s, 1H), 11.39 (s, 1H).(α)$_D$=−52.3° (c1, MeOH).

Compound 41: Mp 142–145° C. $^1$H-NMR (DMSO-d$_6$) δ: 2.70 (s, 3H), 2.71 (s, 3H), 2.95 (s, 3H), 3.36–3.41 (m, 4H), 3.62–3.65 (m, 1H), 3.76–3.88 (m, 4H), 4.20–4.21 (m, 1H), 4.30–4.32 (m, 1H), 4.49 (d, J=13.0 Hz, 3H), 4.59 (d, J=13.0 Hz, 1H), 4.89–5.79 (br, 2H), 7.20–7.23 (m, 2H), 7.51–7.53 (br, 2H), 7.77 (s, 2H), 7.99 (s, 1H), 10.77 (brs, 1H).

Compound 43: $^1$H-NMR (DMSO-d$_6$) δ: 2.23 (s, 3H), 2.95 (s, 3H), 3.03 (ABq, J=16.9 Hz, 2H), 3.53 (d, J=14.3 Hz, 1H), 3.65–3.66 (m, 2H), 3.76–3.77 (m, 1H), 4.0–4.04 (m, 1H), 4.08 (s, 1H), 4.49 (ABq, J=13.0 Hz, 2H), 7.13 (d, J=8.0 Hz, 2H), 7.34 (d, J=8.0 Hz, 2H), 7.75 (s, 2H), 7.97 (s, 1H), 11.27 (s, 1H), 11.41 (s, 1H).

Compound 44: $^1$H-NMR (DMSO-d$_6$) δ: 1.10 (t, J=7.0 Hz, 3H), 2.24 (s, 3H), 2.94–3.11 (m, 3H), 3.30–3.32 (m, 1H), 3.51–4.43 (m, 6H), 4.48 (ABq, J=13.0 Hz, 2H), 7.13 (d, J=8.0, 2H), 7.35 (d, J=8.0, 2H), 7.75 (s, 2H), 7.97 (s, 1H), 11.28 (s, 2H), 11.42 (s, 1H).

Compound 45: $^1$H-NMR (DMSO-d$_6$) δ: 1.10 (t, J=7.0 Hz, 3H), 2.96–3.13 (m, 3H), 3.30–3.31 (m, 1H), 3.50–4.07 (m, 5H), 4.09–4.10 (m, 1H), 4.47 (ABq, J=13.0 Hz, 2H), 7.12–7.15 (m, 2H), 7.52–7.54 (m, 2H), 7.71 (s, 2H), 7.97 (s, 1H), 11.28 (s, 1H), 11.43 (s, 1H).

Compound 46: $^1$H-NMR (DMSO-d$_6$) δ: 0.83 (t, J=7.0 Hz, 3H), 1.49–1.62 (m, 2H), 2.97–3.83 (m, 9H), 4.10–4.11 (m, 1H), 4.49 (ABq, J=13.0 Hz, 2H), 7.14–7.16 (m, 2H), 7.51–7.54 (m, 2H), 7.73 (s, 2H), 7.97 (s, 1H), 11.29 (s, 1H), 11.43 (s, 1H).

Compound 47: $^1$H-NMR (DMSO-d$_6$) δ: 1.11–1.15 (m, 6H), 2.81–3.72 (m, 11H), 4.08–4.09 (m, 1H), 4.49 (ABq, J=13.0 Hz, 2H), 7.19 (d, J=8.0 Hz, 2H), 7.37 (d, J=8.0 Hz, 2H), 7.81 (s, 2H), 7.97 (s, 1H), 11.28 (s, 2H), 11.42 (s, 1H).

Compound 48: $^1$H-NMR (DMSO-d$_6$) δ: 2.92–3.77 (m, 13H), 4.06–4.07 (m, 1H), 4.50 (ABq, J=13.0 Hz, 2H), 6.88 (d, J=8.0 Hz, 2H), 7.37 (d, J=8.0 Hz, 2H), 7.78 (s, 2H), 7.97 (s, 1H), 11.27 (s, 2H), 11.40 (s, 1H).

Compound 49: $^1$H-NMR (DMSO-d$_6$) δ: 1.10 (t, J=7.0 Hz, 3H), 2.96–3.81 (m, 9H), 4.07–4.08 (m, 1H), 4.47 (ABq, J=13.0 Hz, 2H), 7.25–7.36 (m, 3H), 7.48–7.50 (m, 2H), 7.73 (s, 2H), 7.97 (s, 1H), 11.28 (s, 1H), 11.43 (s, 1H).

Compound 50: $^1$H-NMR (DMSO-d$_6$) δ: 2.25 (s, 3H), 2.91–3.10 (m, 5H), 3.58–3.84 (m, 1H), 4.07–4.09 (m, 1H), 4.48 (ABq, J=13.0 Hz, 2H), 7.05–7.29 (m, 4H), 7.72 (s, 2H), 7.97 (s, 1H), 11.28 (s, 1H), 11.45 (s, 1H).

Compound 51: $^1$H-NMR (DMSO-d$_6$) δ: 1.08–1.13 (m, 3H), 2.50–3.75 (m, 12H), 4.08–4.09 (m, 1H), 4.48 (ABq, J=13.0 Hz, 2H), 7.16 (d, J=8.0 Hz, 2H), 7.36 (d, J=8.0 Hz, 2H), 7.78 (s, 2H), 7.97 (s, 1H), 11.28 (s, 1H), 11.43 (s, 1H).

Compound 52: $^1$H-NMR (DMSO-d$_6$) δ: 1.09 (t, J=7.0 Hz, 3H), 2.94–3.78 (m, 12H), 4.01–4.02 (m, 1H), 4.51 (ABq, J=13.0 Hz, 2H), 6.88 (d, J=8.0 Hz, 2H), 7.37 (d, J=8.0 Hz, 2H), 7.79 (s, 2H), 7.97 (s, 1H), 11.25 (s, 2H), 11.38 (s, 1H).

Example 2

Binding Assay for Human NK1 Receptors

A supernatant solution was removed from a culture flask of human NK1-CHO confluent cells, and the cells were detached and collected with a trypsin (0.25%)-EDTA (1 mmol/L) solution (GIBCO). The collected cells were washed once with buffer A (pH 7.5, 50 mmol/L Tris-HCl buffer containing 150 mmol/L NaCl and 0.02% BSA) by centrifugation (1000 rpm, 5 minutes). The number of cells was adjusted and the cells were then resuspended in an assay buffer (buffer A containing 0.04 mg/mL bacitracin (SIGMA), 4 microgram/mL leupeptin (SIGMA), 4 microgram/mL chymostatin (SIGMA) and 4 microgram/mL phosphoramidon (SIGMA)). Human NK1-CHO cells ($10^6$ cells/tube, 0.1 mL) were placed in a tube (TPX-12, Maruemu) containing 0.3 mL of assay buffer (system of 0.5 mL). To the tube, 0.05 mL hot solution of ($^3$H)-Sar$^9$-SP (final concentration 0.3 nmol/L) and 0.05 mL of a tested compound were added. The mixture was stirred and then incubated for 60 minutes at room temperature. After the reactions were terminated, the mixtures were filtered through a GF/B filter (25 mm diameter, Whatman) presoaked in 0.1% polyethyleneimine p-70 (WAKO) in advance. The filter was washed with buffer A (4 mL×3) and dried overnight at 60° C. in a vial. Then 10 mL of scintillator solution (AL-1, toluene base, DOJINDO) were added to each vial and the radioactivity (dpm) retained on the filters was measured by a liquid scintillation counter (5 minutes/vial).

Nonspecific binding was estimated by the radioactivity (dpm) in the presence of 0.01 mmol/L concentration of the Substance P instead of the tested compound. All determinations were carried out at least 3 times in duplicate. IC$_{50}$ values were calculated by probit methods (Statistical Library II, Yukms), of which an example of the result is shown in Table 1. The compounds of the present invention showed very strong antagonistic activity in the binding assay on CHO cells expressing human NK1 receptors:

TABLE 1

| Compound No. | IC$_{50}$ (nmol/L) |
|---|---|
| 12 | 1.5 |
| 26 | 0.04 |
| 32 | 0.24 |
| 42 | 30.0 |

Example 3

In vivo Antagonistic Effects on Tachykinin Receptor

The compounds of the present invention and synthesized LY-303870 were suspended or dissolved in 0.5% sodium carboxymethylcellulose solution, and orally administered at the dose of 5 mL/kg. to male Hartley SPF guinea pigs of 6 week age.

Guinea pigs, sheared of fur, were anesthetized with ether and 1% Evan Blue dye in physiological saline (1 mL/500 g b.w.) was injected into their fore-leg intravenously. Immediately after the dye injection, SP (1 pmol/site), NKA (100 pmol/site) and NKB (100 pmol/site) in physiological saline were injected dorsal intradermally (0.05 mL/site) whereby the reaction of increase of vascular permeability was induced. Half an hour after tachykinin challenge, the animals were sacrificed by decapitation and bloodletting, and the dorsal skin was removed and the amount of transuded blue dye thereof was measured. Namely, the blue dyed sites were punched out using a punch for leather (16 mm diameter), of which 2 pieces were allowed to stand at 37° C. overnight in a covered tube with addition of 1 mL of 2 mol/L KOH solution. After stirring well, 6 mL of a mixture of 2 mol/L H$_3$PO$_4$ solution and acetone (1:3) were added thereto and Evans Blue dye was extracted by vigorous shaking for 10 minutes. After the precipitate was filtered off, the absorbance of the filtrate was measured at 620 nm with a spectrophotometer and the amount of dye was determined from the calibration curve. Nonspecific reaction was estimated from the amount of transuded dye by the injection of physiological saline. The significant difference in the average values between the control group and the test compound-treated group was calculated by means of a Student's t-test or Dunnett's test (Statistical Library I, two-sided test, Yukms).

The tested compounds were orally administered at a dose of 10 mg/kg at various points from 30 min to 8 hrs before the induction of tachykinin-induced increase of vascular permeability. An example of the results is shown in Table 2 (* and ** stand for the significant difference of $p<0.05$ and $p<0.01$ respectively compared to control). The inhibitory effect by Compound 26 of the present invention against tachykinin-induced increase of vascular permeability was much stronger than that of LY-303870 (CAS.RN= 170566–84–4) which has been reported as a tachykinin antagonist:

TABLE 2

| Time from administration to induction | | Substance P (1 pmole/site) | | Neurokinin A (100 pmole/site) | | Neurokinin B (100 pmole/site) | |
|---|---|---|---|---|---|---|---|
| Test Drug | (hr) | n | Mean ± S.E. | n | Mean ± S.E | n | Mean ± S.E |
| Control |  | 10 | 20.5 ± 1.6 | 10 | 20.4 ± 4.4 | 10 | 21.6 ± 2.1 |
| Compound 26 | 0.5 | 8 | 6.2 ± 1.5** | 8 | 3.6 ± 0.7** | 8 | 1.4 ± 0.9** |
|  | 1 | 8 | 1.4 ± 0.6** | 8 | 1.0 ± 0.5** | 8 | 0.1 ± 0.1** |
|  | 2 | 8 | 4.3 ± 0.9** | 8 | 2.6 ± 1.4** | 8 | 0.5 ± 0.4** |
|  | 4 | 8 | 4.9 ± 1.3** | 8 | 3.6 ± 2.6** | 8 | 1.0 ± 0.4** |
|  | 8 | 8 | 11.9 ± 2.4** | 8 | 10.1 ± 3.3 | 8 | 9.4 ± 1.6** |
| LY-303870 | 0.5 | 8 | 6.3 ± 2.1** | 8 | 5.3 ± 2.3** | 8 | 2.0 ± 1.2** |
|  | 1 | 8 | 7.8 ± 2.5** | 8 | 5.8 ± 1.9** | 8 | 5.0 ± 2.2** |
|  | 2 | 8 | 17.0 ± 3.4 | 8 | 14.5 ± 5.0 | 8 | 12.0 ± 3.2* |
|  | 3 | 8 | 12.2 ± 2.2** | 8 | 11.1 ± 4.3 | 8 | 7.7 ± 1.8** |
|  | 4 | 8 | 14.4 ± 0.9** | 8 | 10.8 ± 3.4 | 8 | 13.6 ± 1.1** |

As shown in Table 1, a piperazine derivative of the present invention exhibited an excellent activity as a tachykinin receptor antagonist, which belongs of the strongest group as ever reported until now. Moreover, the compound showed a strong inhibitory action against tachykinin-induced increase of vascular permeability in an in vivo test (Table 2). The compound of this invention exhibited a preferred transfer into blood, and a long half-life in blood was observed in pharmacokinetic tests of oral administration to rats or guinea pigs. Moreover, it was very stable in blood plasma of various animals. As above-mentioned, piperazine derivatives of the present invention having novel chemical structure exhibit an excellent tachykinin receptor antagonistic activity and a favorable behavior in vivo, therefore, the compounds have desirable properties as pharmaceuticals and their usefulness is quite high. The compounds of the present invention may be used to substantially reduce the activity of tachykinins in the blood by blocking their access to tachykinin receptors.

In embodiments of the present invention, a disease or condition associated with at least one tachykinin may be treated by determining the serum tachykinin value of a patient and administering to a patient in need of such treatment a pharmaceutically effective amount of at least one 2-phenylpiperazine derivative according to formula (I) or a pharmaceutically acceptable salt, hydrate, or complex thereof to substantially suppress the serum tachykinin value. The tachykinin level, such as the amount of one or more of Substance P (SP), neurokinin A (NKA) and neurokinin B (NKB), can be determined using conventional tests or quantitative analyses. Thus, in embodiments of the present invention, diseases or conditions associated with at least one tachykinin, such as Substance P, may be treated in a patient in need of such treatment by measuring the serum tachykinin value, determining whether the serum tachykinin value or level of the patient is present at an abnormal level, and administering a 2-phenylpiperazine derivative of the present invention to suppress the tachykinin value or level to a normal level so as to alleviate symptoms of the disease or condition.

We claim:

1. A 2-phenylpiperazine derivative represented by the following formula (I) or a pharmaceutically acceptable salt, thereof, said 2-phenylpiperazine derivative being represented by the formula (I):

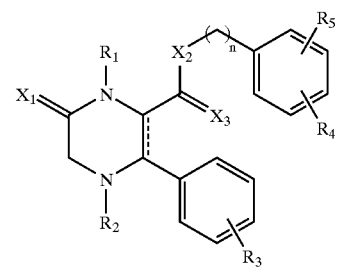

wherein each of $X_1$ and $X_3$ is oxygen or two hydrogen atoms, $X_2$ is O, NH, $NCH_3$, or $CH_2$, n is an integer of 0 or 1, $R_1$ is hydrogen or lower alkyl and $R_2$ is hydrogen, cyano, tetrazolyl, aminotriazolyl, mesyl, t-butoxycarbonyl, or lower alkyl, wherein when $R_2$ is lower alkyl, the lower alkyl may be optionally substituted with a substituent selected from the following substituents (a) to (j) and/or oxo, (a) triazolonyl,
(b) tetrazolyl,
(c) dimethylaminomethyltriazolyl;
(d) phosphotriazolonyl,
(e) pyridyl,
(f) dimethylamino,
(g) cyano, (h) pyrrolidino,
(i) amino,
(j) phenyl, $R_3$ is hydrogen, halogen, lower alkyl or lower alkoxy, each of $R_4$ and $R_5$ is hydrogen, lower alkoxy or trifluoromethyl, and a broken line indicates a single or double bond.

2. A 2-phenylpiperazine derivative according to claim 1 wherein $X_1$ is oxygen.

3. A 2-phenylpiperazine derivative according to claim 2 wherein $X_2$ is oxygen.

4. A 2-phenylpiperazine derivative according to claim 3 wherein $X_3$ is two hydrogen atoms.

5. A 2-phenylpiperazine derivative according to claim 4 wherein n is an integer of 1.

6. A 2-phenylpiperazine derivative according to claim 5 wherein $R_1$ is methyl.

7. A 2-phenylpiperazine derivative according to claim 6 wherein $R_2$ is triazolonylmethyl.

8. A 2-phenylpiperazine derivative according to claim 7 wherein $R_3$ is hydrogen.

9. A 2-phenylpiperazine derivative according to claim 8 wherein $R_4$ is substituted at the m-position.

10. A 2-phenylpiperazine derivative according to claim 9 wherein $R_4$ is trifluoromethyl.

11. A 2-phenylpiperazine derivative according to claim 10 wherein $R_5$ is substituted at the m-position.

12. A 2-phenylpiperazine derivative according to claim 11 wherein $R_5$ is trifluoromethyl.

13. A 2-phenylpiperazine derivative according to claim 1 wherein $R_2$ is lower alkyl which is substituted with oxo.

14. A 2-phenylpiperazine derivative according to claim 13 wherein $R_2$ is lower alkyl which is substituted with both an oxo and a triazolonyl substituent.

15. (5S,6S)-6-(3,5-Bis(trifluoromethyl)benzyloxymethyl)-1-methyl-4-(5-oxo-4,5-dihydro-1H-(1,2,4)triazol-3-ylmethyl)-5-phenylpiperazin-2-one.

16. A pharmaceutical composition comprising at least one 2-phenylpiperazine derivative or a pharmaceutically acceptable salt, thereof according to claim 1 in a pharmaceutically effective amount, and a pharmaceutically acceptable carrier.

17. A pharmaceutical composition according to claim 16 wherein $X_1$ is oxygen.

18. A pharmaceutical composition according to claim 16 wherein said at least one 2-phenylpiperazine derivative comprises (5S,6S)-6-(3,5-Bis(trifluoromethyl)benzyloxymethyl)-1-methyl-4-(5-oxo-4,5-dihydro-1H-(1,2,4)triazol-3-ylmethyl)-5-phenylpiperazin-2-one.

* * * * *